US012636389B2

(12) United States Patent     (10) Patent No.:   US 12,636,389 B2

Lee et al.     (45) Date of Patent:     May 26, 2026

(54) ELECTROLYTIC DEVICES AND METHODS FOR DRY HYDROGEN PEROXIDE PRODUCTION

(71) Applicant: Synexis LLC, Overland Park, KS (US)

(72) Inventors: James D. Lee, Prairie Village, KS (US); John Ness-Hunkin, Kansas City, MO (US); David M. Schut, Overland Park, KS (US); Zachary N. Martin, Overland Park, KS (US)

(73) Assignee: Synexis LLC, Overland Park, KS (US)

( * ) Notice: Subject to any disclaimer, the term of this patent is extended or adjusted under 35 U.S.C. 154(b) by 903 days.

(21) Appl. No.: 17/285,028

(22) PCT Filed: Oct. 11, 2019

(86) PCT No.: PCT/US2019/055935

§ 371 (c)(1),
(2) Date: Apr. 13, 2021

(87) PCT Pub. No.: WO2020/077263

PCT Pub. Date: Apr. 16, 2020

(65) Prior Publication Data

US 2021/0340682 A1     Nov. 4, 2021

Related U.S. Application Data

(60) Provisional application No. 62/745,131, filed on Oct. 12, 2018.

(51) Int. Cl.
| | |
|---|---|
| *A61L 2/208* | (2026.01) |
| *A61L 2/14* | (2006.01) |

(Continued)

(52) U.S. Cl.
CPC ................. *A61L 2/208* (2013.01); *A61L 2/14* (2013.01); *A61L 9/22* (2013.01); *F24F 8/30* (2021.01); *A61L 2209/211* (2013.01); *C25B 1/30* (2013.01)

(58) Field of Classification Search
CPC .. C25B 1/30; C25B 9/19; C25B 11/03; C25B 11/031; C25B 11/036; C25B 11/051;

(Continued)

(56) References Cited

U.S. PATENT DOCUMENTS

| | | | | |
|---|---|---|---|---|
| 4,430,176 A | * | 2/1984 | Davison | .................... C25B 1/30 204/284 |
| 5,573,577 A | * | 11/1996 | Joannou | ................. B03C 3/155 96/96 |

(Continued)

FOREIGN PATENT DOCUMENTS

| | | |
|---|---|---|
| CN | 109589441 A1 | 4/2019 |
| EP | 0 306301 | 3/1989 |

(Continued)

OTHER PUBLICATIONS

Nickel Alloys in Today's Electronics Industry © 1987 Nickel Institute (Year: 1987).*

(Continued)

*Primary Examiner* — Luan V Van
*Assistant Examiner* — Alexander R. Parent
(74) *Attorney, Agent, or Firm* — Hovey Williams LLP

(57) ABSTRACT

The present disclosure provides for and includes electro-catalytic devices and methods for the production of Dry Hydrogen Peroxide (DHP), a non-hydrated, gaseous form of hydrogen peroxide.

24 Claims, 19 Drawing Sheets

100

120 Cross-section

(51) Int. Cl.
*A61L 9/22* (2006.01)
*C25B 1/30* (2006.01)
*F24F 8/30* (2021.01)

(58) Field of Classification Search
CPC ... C25B 11/055; C25B 11/056; C25B 11/077;
C25B 11/0771; C25B 11/0773; C25B
11/0775; A61L 2/035; A61L 2/208; A61L
9/22; A61L 9/205; A61L 2/14; A61L
2209/211; F24F 8/30; F24F 8/192; B03C
3/38
USPC .............. 205/466; 204/284; 422/174; 96/96
See application file for complete search history.

(56) References Cited

U.S. PATENT DOCUMENTS

| | | | |
|---|---|---|---|
| 5,696,198 A | 12/1997 | Chereisky et al. | |
| 5,933,702 A | 8/1999 | Goswami | |
| 5,948,355 A | 9/1999 | Fujishima et al. | |
| 6,051,117 A * | 4/2000 | Novak | C25B 13/00 205/333 |
| 6,805,732 B1 * | 10/2004 | Billiotte | A61L 9/22 264/129 |
| 7,541,509 B2 * | 6/2009 | Sigmund | A61L 9/205 588/299 |
| 7,854,900 B2 * | 12/2010 | Takeda | A61L 9/22 422/186.04 |
| 7,988,923 B2 | 8/2011 | Fink et al. | |
| 8,012,412 B2 | 9/2011 | James et al. | |
| 8,658,101 B1 | 2/2014 | Burnett | |
| 8,877,046 B2 | 11/2014 | Ellis | |
| 9,283,295 B2 | 3/2016 | Fink et al. | |
| 9,295,746 B2 | 3/2016 | Ellis | |
| 9,433,691 B2 | 9/2016 | Eide et al. | |
| 9,839,901 B2 | 12/2017 | Ellis et al. | |
| 2005/0191205 A1 | 9/2005 | Uslenghi et al. | |
| 2007/0023294 A1 * | 2/2007 | Trimmer | C25B 1/30 205/466 |
| 2007/0153363 A1 | 7/2007 | Gruner | |
| 2008/0075627 A1 * | 3/2008 | Garin | A61L 9/205 422/4 |
| 2008/0170971 A1 * | 7/2008 | Bergeron | A61L 9/22 422/186.04 |
| 2009/0041617 A1 | 2/2009 | Lee | |
| 2009/0291844 A1 * | 11/2009 | Hou | A61L 2/232 502/160 |
| 2011/0182772 A1 | 7/2011 | Holt | |
| 2011/0182773 A1 | 7/2011 | Holt | |
| 2011/0183598 A1 | 7/2011 | Holt | |
| 2012/0182666 A1 | 7/2012 | Kinlen et al. | |
| 2015/0125356 A1 * | 5/2015 | Miyamoto | A61L 9/22 422/186.07 |
| 2016/0367712 A1 * | 12/2016 | Robert | A61L 9/22 |
| 2018/0112318 A1 * | 4/2018 | Kim | C25B 11/055 |
| 2018/0345210 A1 * | 12/2018 | Miyake | A61L 9/22 |
| 2020/0368713 A1 | 11/2020 | Holt | |
| 2021/0038755 A1 | 2/2021 | Eide | |
| 2021/0228762 A1 | 7/2021 | Eide et al. | |
| 2021/0346565 A1 | 11/2021 | Woodbridge | |

FOREIGN PATENT DOCUMENTS

| | | |
|---|---|---|
| EP | 0978690 | 2/2000 |
| EP | 1 491 218 | 12/2004 |

| | | | | |
|---|---|---|---|---|
| KR | 2014/0073180 A | 6/2014 | | |
| WO | WO-2012114108 A1 * | 8/2012 | .............. | C25B 1/00 |
| WO | WO 2014/186805 | 11/2014 | | |
| WO | WO 2015/026958 | 2/2015 | | |
| WO | WO-2015171633 A1 * | 11/2015 | .............. | A61L 9/14 |
| WO | WO 2016/172223 | 10/2016 | | |
| WO | WO 2016/176486 | 11/2016 | | |
| WO | WO 2018/129537 | 7/2018 | | |

OTHER PUBLICATIONS

Rumble ed. "Thermal and Physical Properties of Pure Elemental Metals" in CRC Handbook of Chemistry and Physics, 105th Edition (Internet Version 2024), CRC Press/Taylor & Francis, Boca Raton, FL (Year: 2024).*

MatWeb ("304 Stainless Steel" 2025 Web www.matweb.com/search/datasheet.aspx?MatGUID=abc4415b0f8b490387e3c922237098da&ckck=1) (Year: 2025).*

Lian et al. ("Decomposition of high-level ozone under high humidity over Mn—Fe catalyst: The influence of iron precursors" Catalysis Communications 59 (2015) 156-160) (Year: 2015).*

Radhakrishnan et al. "Electron Transfer Effects in Ozone Decomposition on Supported Manganese Oxide" J. Phys. Chem. B 2001, 105, 4245-4253 (Year: 2001).*

Mathew et al. "Mesoporous Ferrihydrite-Based Iron Oxide Nanoparticles as Highly Promising Materials for Ozone Removal" Angew. Chem. Int. Ed. 2011, 50, 7381-7384 (Year: 2011).*

Agalloco et al., "Overcoming Limitations of Vaporized Hydrogen Peroxide," *Pharmaceutical Technology,* 37(9):1-7 (2013).

Blake et al., "Application of the Photocatalytic Chemistry of Titanium Dioxide to Disinfection and the Killing of Cancer Cells," Separation and Purification Methods 28(1):1-50 (1999).

"Development of a High-performance Photocatalyst that is Surface-treated with Cesium," available on the internet at https://www(dot)aist(dot)go(dot)jp/aist_e/list/latest_research/2010/20100517/20100517.html (2010).

International Search Report issued Jan. 2, 2020 in International Appln. No. PCT/US2019/055935.

Kahnert et al., "Decontamination with vaporized hydrogen peroxide is effective against *Mycobacterium tuberculosis,*" *Lett. Appl. Microbiol.* 40(6):448-52 (2005).

Kim et al., "Photocatalytic Activity of $TiO_2$ Films Preserved under Different Conditions: The Gas-Phase Photocatalytic Degradation Reaction of Trichloroethylene," *Journal of Catalysis* 194(2):484-486 (2000).

Roy et al., "Crytsl Structure and Band Gap Engineering in Polyoxometalate Based Inorgantic-Organic Hybrids," *Inorg. Chem.,* 55(7), 3364-3377 (2016).

Shon et al., "Visible Light Responsive Titanium Dioxide ($TiO_2$)—a review" available at epress.lib.uts.edu.au (2008).

Sugihara et al., "Development of a Visible Light Responsive Photocatalyst using Tungsten Oxide under Indoor Lighting," National Institute of Advanced Industrial Science and Technology (AIST) (2008).

Tukenmez, "Tungsten Oxide Nanopowders and Its Catalytic Activity under Visible Light Irradiation," Thesis, Department of Molecular Biology, Umea University, Sweden, (2013) available on the internet at www(dot)diva-portal(dot)org/smash/get/diva2:643926/FULLTEXT01.pdf (2013).

Office Action of Corresponding Israeli Patent Application 28218 dated Sep. 2, 2022.

* cited by examiner

120 Cross-section 125   130   135

Figure 9:
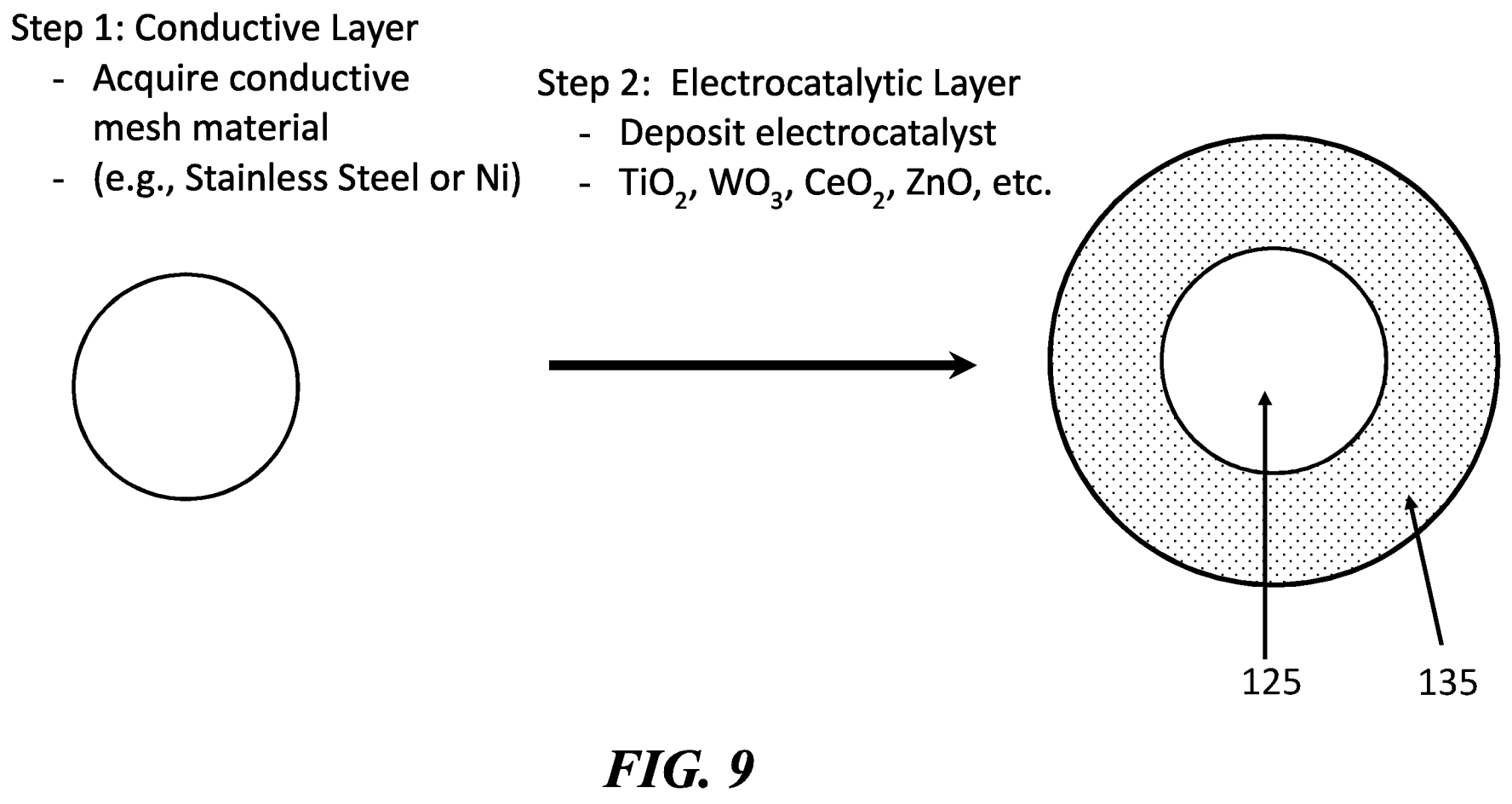

Step 1: Conductive Layer
- Acquire conductive mesh material
- (e.g., Stainless Steel or Ni)

Step 2: Electrocatalytic Layer
- Deposit electrocatalyst
- $TiO_2$, $WO_3$, $CeO_2$, ZnO, etc.

Step 1: Conductive Layer
- Acquire conductive mesh material
- (e.g., Stainless Steel or Ni)

125

Step 2 (Adhesive Layer):
- Add Silane Coupling Agent
- $H_2N-CH_2CH_2CH_2-Si(OR)_3$
- $R = -H, -CH_3, -CH_2CH_3$ Step 3: Catalytic Layer
- Deposit electrocatalyst
- $TiO_2$, $WO_3$, $CeO_2$, $ZnO$, etc.

125  130  135

Step 1: Conductive Layer
- Acquire mesh material
- (e.g., Ag or Cu)

Step 2: Conductive Layer
- Electroplate (Ni, Cr) or
- Electroless plate (Ni)

Step 3 (Adhesive Layer):
- Add Silane Coupling Agent
- $H_2N\text{-}CH_2CH_2CH_2\text{-}Si(OR)_3$
- $R = \text{-H, -}CH_3, \text{-}CH_2CH_3$ Step 4: Catalytic Layer
- Deposit electrocatalyst
- $TiO_2$, $WO_3$, $CeO_2$, ZnO, etc.

Step 1: Non-Conductive Layer
- Acquire mesh material
- Natural fiber
- Plastic

Step 2: Conductive Layer
- Electroless plate (Ni)

Step 3: Catalytic Layer
- Deposit electrocatalyst
- $TiO_2$, $WO_3$, $CeO_2$, ZnO, etc.

140

125

140

135

125

140

Step 1: Non-Conductive Layer
- Acquire mesh material
- Natural fiber
- Plastic

Step 2: Conductive Layer
- Electroless plate (Ni)

Step 3 (Adhesive Layer):
- Add SCA
- HS-CH$_2$CH$_2$CH$_2$-Si(OR)$_3$
- R = -H, -CH$_3$, -CH$_2$CH$_3$ Step 4: Catalytic Layer
- Deposit electrocatalyst
- TiO$_2$, WO$_3$, CeO$_2$, ZnO, etc.

ELECTROLYTIC DEVICES AND METHODS FOR DRY HYDROGEN PEROXIDE PRODUCTION

CROSS-REFERENCE TO RELATED APPLICATIONS

This application is a U.S. National Phase application of International Application No. PCT/US2019/055935 filed Oct. 11, 2019, which claims priority from U.S. Provisional Patent Application Ser. No. 62/745,131, filed Oct. 12, 2018, the entireties of which are herein incorporated by reference.

FIELD OF THE INVENTION

The present disclosure relates to methods and devices for the production of Dry Hydrogen Peroxide (DHP) gas. More specifically, this disclosure relates to a new architecture that generates DHP gas through an electro-catalytic process. This new method of generating DHP provides for new applications of DHP gas due to greatly improved efficiency, low power requirements and scalability.

BACKGROUND OF THE INVENTION

A number of U.S. patents describe Dry Hydrogen Peroxide (DHP) gas. DHP was first described in United States Patent Publication No. US 2009/0041617 published Feb. 12, 2009 ("the '617 Publication"). Because photocatalysts can generate hydroxyl radicals from adsorbed water when activated by ultraviolet light of sufficient energy, they have been demonstrated for use in the production of DHP for release into the environment when applied in the gas phase. Prior to the development of DHP generating devices as discussed below, applications of photocatalysis focused on the generation of a plasma containing many different reactive chemical species including hydrogen peroxide. Since the majority of the chemical species in the photocatalytic plasma are reactive with hydrogen peroxide, they inhibit the production of hydrogen peroxide gas by means of reactions that destroy hydrogen peroxide. Also, any organic gases that are introduced into the plasma inhibit hydrogen peroxide production both by direct reaction with hydrogen peroxide and by the reaction of their oxidized products with hydrogen peroxide. DHP devices differ from traditional photocatalytic reactors in that the DHP is removed from the plasma and directed away the device.

The '617 publication discloses the photocatalytic production of DHP using a flow of ambient air through an air permeable catalyst coated mesh, termed a "sail." Under operation, the absorption of photons at certain catalyst defined wavelengths generates a reactive ionized region called a "plasma" at the catalyst's surface. Plasmas consist of positive ions and free electrons as well as hydroxyl radicals, hydroxyl ions, superoxides, ozone ions, hydrogen peroxide, and hydrogen ions. These components are prepared in situ on the surface of the illuminated catalyst from the oxygen and water present in ambient air. By flowing ambient air through the air permeable substrate, components of the plasma are removed and directed away from the catalytic surface. Thus, the flow of air removes the reactive species before they can be consumed. Away from the device, nearly all of the reactive species are consumed or degraded, leaving the relatively stable hydrogen peroxide to persist and accumulate in the area outside the device.

The prior recognition of these plasmas led to the development of various photocatalytic air purifying devices designed to react with pollutants and contaminants present in a flow of air with the plasma. Examples of such photocatalytic air purifiers include those described in U.S. Pat. No. 7,988,923 issued Aug. 2, 2011, to Fink et al., U.S. Pat. No. 9,283,295 issued Mar. 15, 2016, to Fink et al., U.S. Patent Publication No. 2005/0191205 by Uslenghi et al. published Sep. 1, 2005, U.S. Pat. No. 5,933,702, issued Aug. 3, 1999, to Goswami, U.S. Pat. No. 8,658,101, issued Feb. 25, 2014 to Burnett, and U.S. Pat. No. 5,948,355, issued Sep. 7, 1999, to Fujishima et al. The prior art photocatalytic devices that are designed to oxidize contaminants on the catalytic surface inside an enclosure as contaminated air is passed through.

In contrast to prior art photocatalytic air purifiers, DHP generating devices are designed to prepare hydrogen peroxide gas and direct it outside of the device and into the surrounding environment. In an enclosed environment, DHP produced by the devices accumulates and acts in a continuous manner to control microbes. As DHP is produced at low levels (generally less than 0.1 parts per million or 100 parts-per-billion), early methods of detection relied on measuring the amount of hydrogen peroxide in a larger volume of air and then calculating the actual concentration. See the '617 Publication at paragraph [0062]. The '617 Publication first demonstrated the production of DHP using a photocatalytic device and demonstrated its effectiveness on the growth and survival of bacteria, fungi, and viruses. The devices of the '617 publication provided for the continuous control of microbes on air and surfaces when the DHP is contained and allowed to accumulate in an environment. DHP was subsequently shown to be effective in a variety of applications and environments. International Patent Application No. PCT/US2014/038652, published as International Patent Publication No. WO 2014/186805, discloses the effectiveness and use of DHP for the control of arthropods, including insects and arachnids. International Patent Application No. PCT/US2014/051914, published Feb. 26, 2015, as International Patent Publication No. WO2015/026958, discloses the beneficial effects of DHP on respiratory health, including increased resistance to infection and increased hypothiocyanate ions in mammalian lungs. International Patent Application No. PCT/US2015/029276, published Nov. 12, 2015, as International Patent Publication No. WO 2015/171633, discloses improvements to DHP generating devices including improved sails and catalysts. International Patent Application No. PCT/US2016/028457, published Oct. 27, 2016, as International Patent Publication No. WO 2016/172223, discloses an application of DHP to clean rooms. International Patent Application No. PCT/US2016/029847, published Nov. 3, 2016, as International Patent Publication No. WO 2016/176486, discloses methods of use of DHP in agricultural production, transport, and storage. International Patent Application No. PCT/US2018/012984, published as International Patent Publication No. WO 2018/129537 on Jul. 12, 2018, discloses the application of DHP to poultry production. The contents of each of the foregoing applications are incorporated herein by reference in their entireties.

Each of the previously filed applications describe a photocatalytic device with an air-permeable substrate structure having a catalyst on its surface, a source of light, and wherein an airflow through the UV light irradiated, catalyst coated air-permeable substrate structure led to the production of DHP with the airflow directing the DHP away from the air permeable substrate and into an environment. While various configurations have been disclosed, the designs rely on the generation of a plasma on the catalytic surface and the removal of DHP molecules from the surface before the DHP can be destroyed by other components present in the plasma. Improvements to the efficiency and operation of the device have included modifications to the catalyst and optimization of the thickness and air-permeability of the substrate structure.

The earlier described DHP generating devices differ significantly from previous photocatalytic devices such as those described in U.S. Pat. No. 7,988,923, issued Aug. 2, 2011, to Fink et al., by providing a morphology that allows the DHP to be removed from the catalytic surface. Other surface based photocatalytic oxidizers are known including European Patent Publication EP 1 491 218 by Huang et al. published Dec. 29, 2004, European Patent Publication No. 0 306301 by Henderson published Mar. 8, 1989, European Patent Publication No. 0978690 by Ikebata et al. published Feb. 9, 2000. These photocatalytic devices differ from DHP generating devices as they are designed and configured to bring contaminants into contact with the photocatalytic surface and its local plasma field. Improvements to the surface based air purifiers and sanitizers are directed to increasing the surface area, increasing plasma density, improving catalytic efficiency and illumination and the like. All of these earlier devices do not direct any active species into the environment but rather generate a dense plasma field inside the device that acts on air flowing through or past the catalytic surface and, in some cases, in a short-lived plasma lobe confined to an area up to two feet immediately outside the device. This lobe effect is both limited and local because the constant application of energy is required to maintain the plasma and prevent its extremely rapid decay into humidity and oxygen.

As noted above, DHP generating devices differ from photocatalytic devices that are designed to oxidize contaminants on the catalytic surface inside an enclosure, including a duct, as contaminated air is passed through. Lacking the morphology for the production of DHP, they provide for the conduction of a stable, active species into the larger environment at great distances from the devices themselves.

The DHP devices previously described are all based on a photocatalytic process. Photocatalytic methods are limited by the amount of energy available (e.g., limited by the intensity of the light) and require a power source for the UV light. Further, in a photocatalytic process, in order to get the best efficiency, each portion of the mesh or sail must be irradiated at equal levels. A similar decrease in efficiency occurs when the sail is illuminated unevenly. An example is where there is less power provided to the edges compared to the center. The devices of the present specification overcome this limitation. Generally, the requirement for a UV light (incandescent or light emitting diode) generally limits the DHP devices to locations that are "on the grid." The present devices are an improvement as they can be run at low power.

Ozonators are another technology that has long been applied. Ozonators produce ozone by various means such as the photolysis of oxygen using UV light of 186 nm and shorter wavelengths, or electrostatically by producing energetic sparks from conductive plates to separate oxygen molecules into individual oxygen atoms, which then combine with oxygen molecules to produce ozone.

Though ozone can disinfect microbes and deodorize air, it is unsafe to use as codified in the United States at 21 CFR 801.415 (a): "Ozone is a toxic gas with no known useful medical application in specific, adjunctive, or preventive therapy. In order for ozone to be effective as a germicide, it must be present in a concentration far greater than that which can be safely tolerated by man and animals." Although this has not prevented the sale of ozonators for these purposes. Government safety restrictions and public wariness of ozonators have simply induced certain manufacturers of these devices to market them using ill-defined and ambiguous terms such as 'activated oxygen" and "friendly air oxidizers".

The present disclosure provides for the first time a method of production DHP using an electrocatalytic process. The devices disclosed provide for a solid state method of generating DHP that is scalable and can be operated at greatly improved efficiency with low power. It further provides for increased efficiency and capacity as ECM sails can comprise activated catalysts nearly all the time.

SUMMARY OF THE INVENTION

The present disclosure provides for, and includes, a device for the production of dry hydrogen peroxide (DHP) comprising an electrically conductive network coated with a catalyst and powered by an electrical power source.

The present disclosure provides for, and includes, a device for the production of dry hydrogen peroxide (DHP) comprising an electrically conductive network coated with a catalyst, an air distribution mechanism, and powered by an electrical power source.

The present disclosure provides for, and includes, a device for the production of dry hydrogen peroxide (DHP) comprising an electrically conductive network comprising a metal meshwork comprising a metal selected from the group consisting of copper, annealed copper, silver, gold, aluminum, tungsten, zinc, nickel, iron, platinum, tin, titanium, grain oriented electrical steel, stainless steel, and nichrome, coated with a catalyst that is a metal oxide selected from the group consisting of titanium dioxide, copper oxide, zinc oxide, iron oxide, tungsten oxide, and mixtures thereof, and powered by an electrical power source.

The present disclosure provides for, and includes, a device for the production of dry hydrogen peroxide (DHP) comprising an electrically conductive network (or mesh) comprising a metal meshwork comprising a metal selected from the group consisting of copper, annealed copper, silver, gold, aluminum, tungsten, zinc, nickel, iron, platinum, tin, titanium, grain oriented electrical steel, stainless steel, and nichrome, coated with a catalyst that is a metal oxide selected from the group consisting of titanium dioxide, copper oxide, zinc oxide, iron oxide, tungsten oxide, and mixtures thereof, an air distribution mechanism, and an electrical power source.

The present disclosure provides for, and includes, a method for producing DHP comprising providing an airflow to a device for the production of dry hydrogen peroxide (DHP) comprising an electrically conductive network coated with a catalyst and powered by an electrical power source, wherein the power source provides a current through the electrically conductive network.

BRIEF DESCRIPTION OF THE DRAWINGS

The present disclosure is disclosed with reference to the accompanying drawings, wherein:

FIGS. 1A to 1E presents images of crystals of titanium dioxide ($TiO_2$) applied to a copper mesh according to the present disclosure. FIG. 1A presents crystals of $TiO_2$ before application to a copper mesh. FIG. 1B presents an image of crystals of $TiO_2$ after exposure to a copper mesh. FIG. 1C presents an image of $TiO_2$ applied to a copper mesh of the present disclosure. FIG. 1D presents an image of the $TiO_2$ after application of a voltage to the copper mesh according Example 5. FIG. 1E presents an image of the crystals removed from the copper mesh after voltage application.

FIG. 8A presents ECM 100 comprising electrically conductive network 110 formed from coated conductors 120 held in a frame 150, said frame 150 having electrical connectors. FIG. 8B presents a diagram of a cross section of a coated conductor 120 having a conductive core material 125, an optional adhesive layer 130, and a catalytic layer 135 (layers not drawn to scale).

FIG. 9 illustrates the preparation of an ECM according to an aspect of the present disclosure. A conductive mesh layer 125, for example stainless steel or nickel, is coated with an electrocatalyst 135 such as $TiO_2$, $WO_3$, $CeO_2$, ZnO, directly on the conductive layers.

Figure 1E:
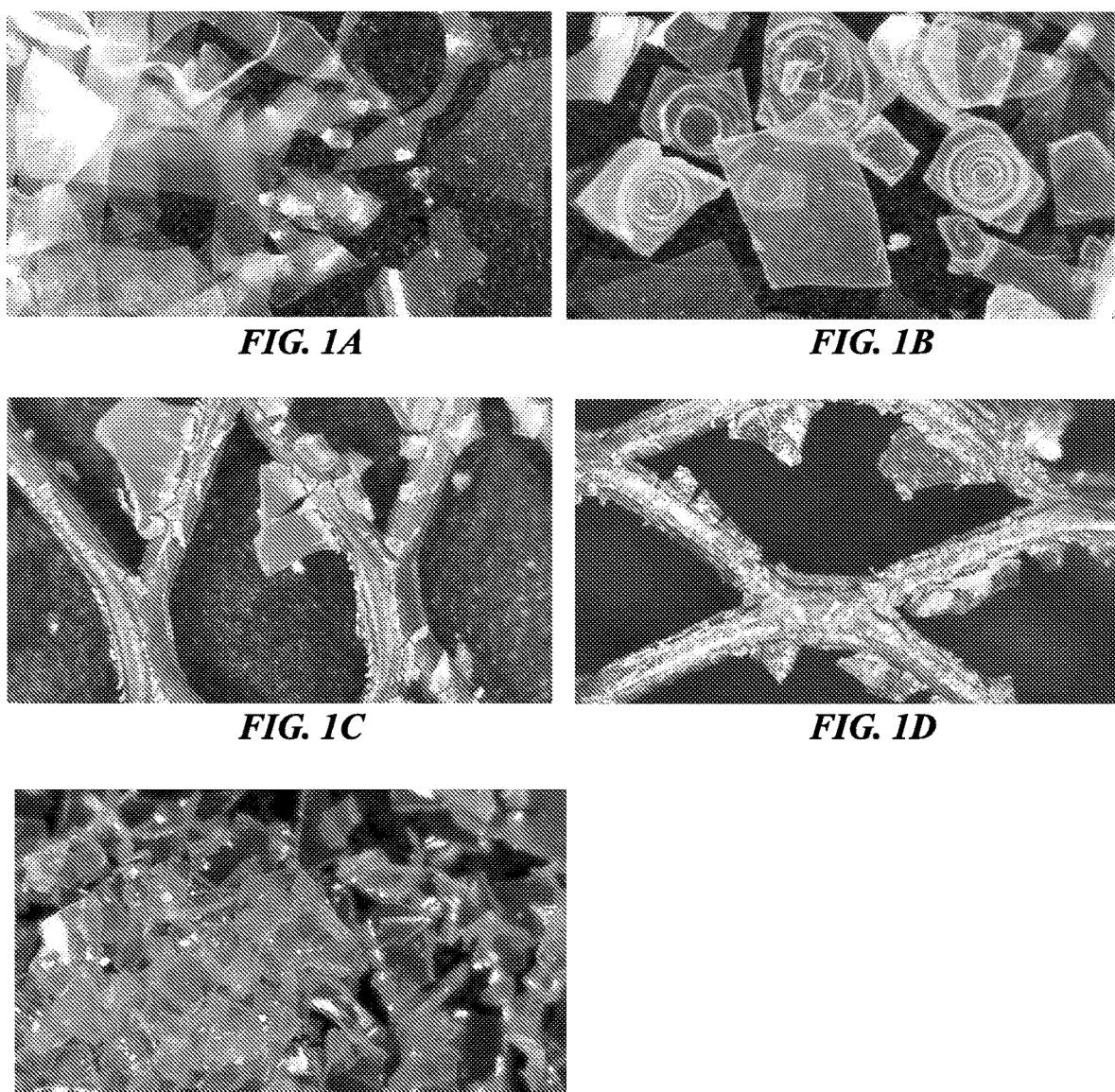
Figure 2A:
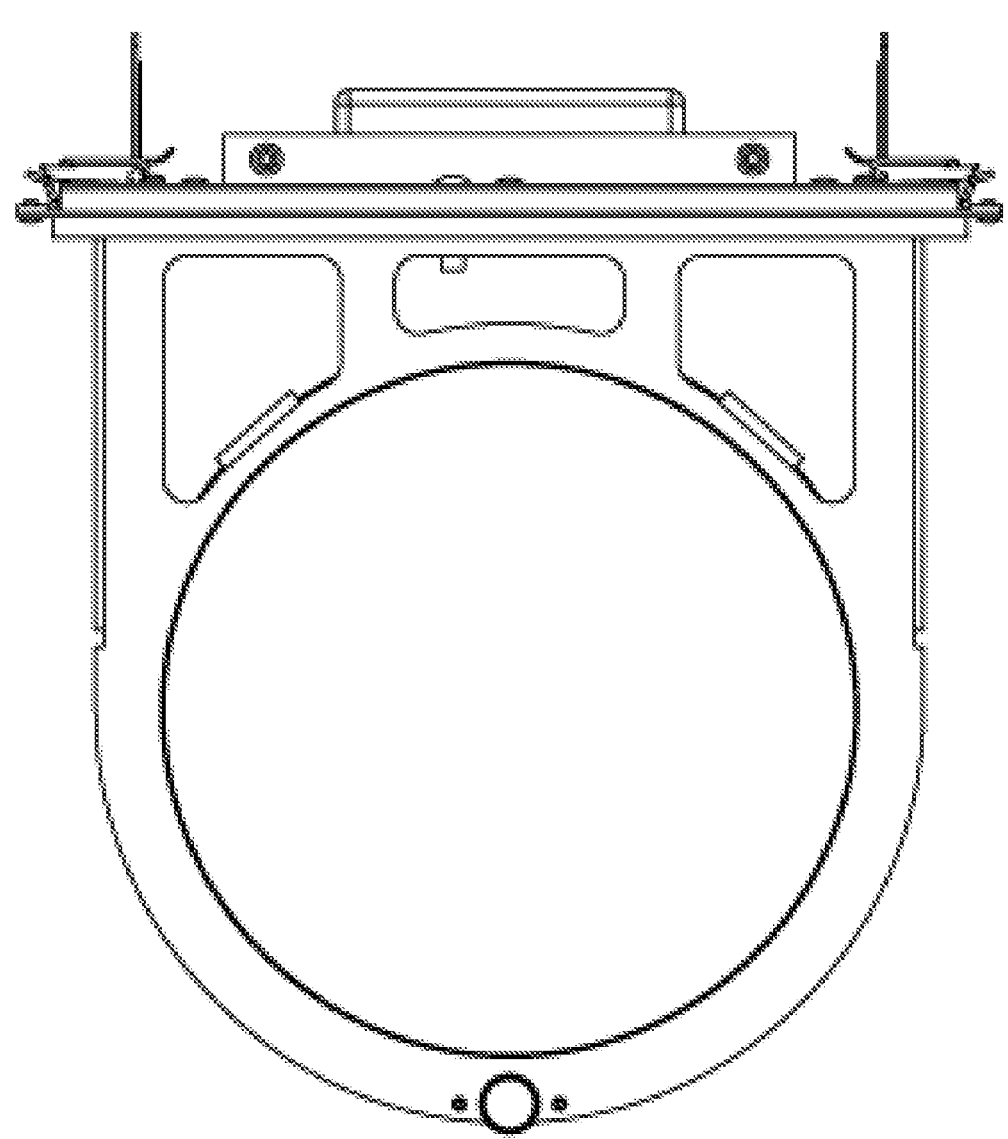
FIG. 2A to 2E are front (A), top (B) bottom (C) right (D) and isometric view (E) of a device of present disclosure.
Figure 2B:
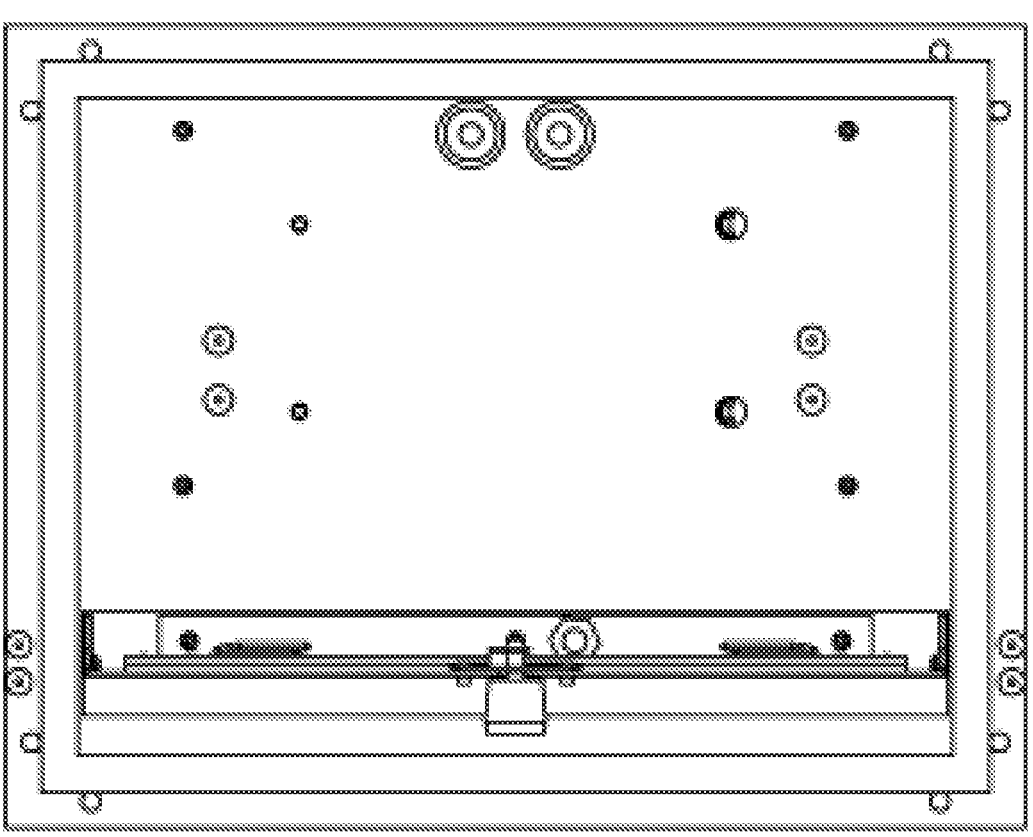
Figure 2C:
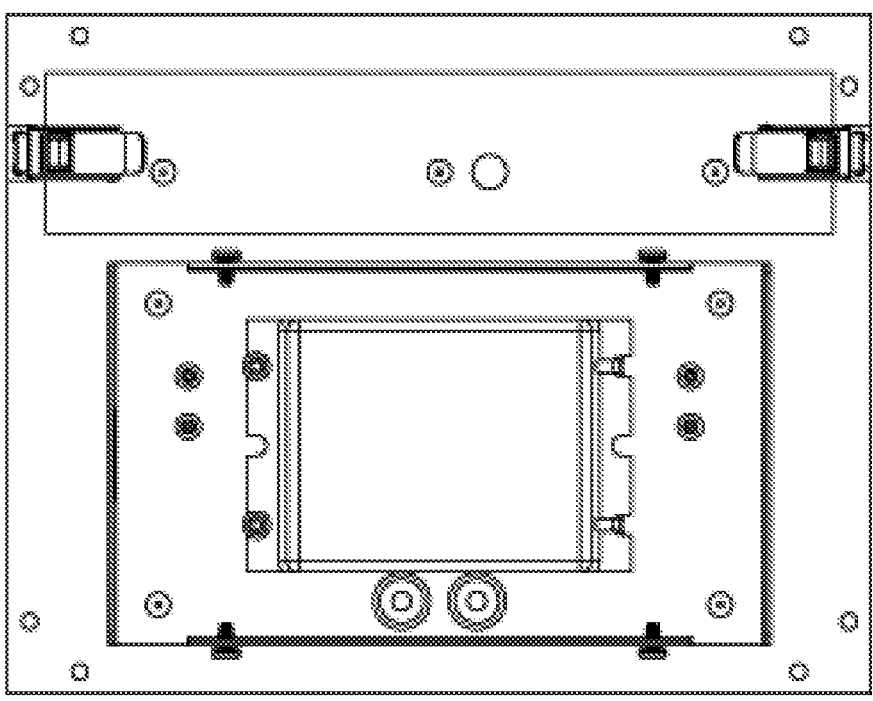
Figure 2D:
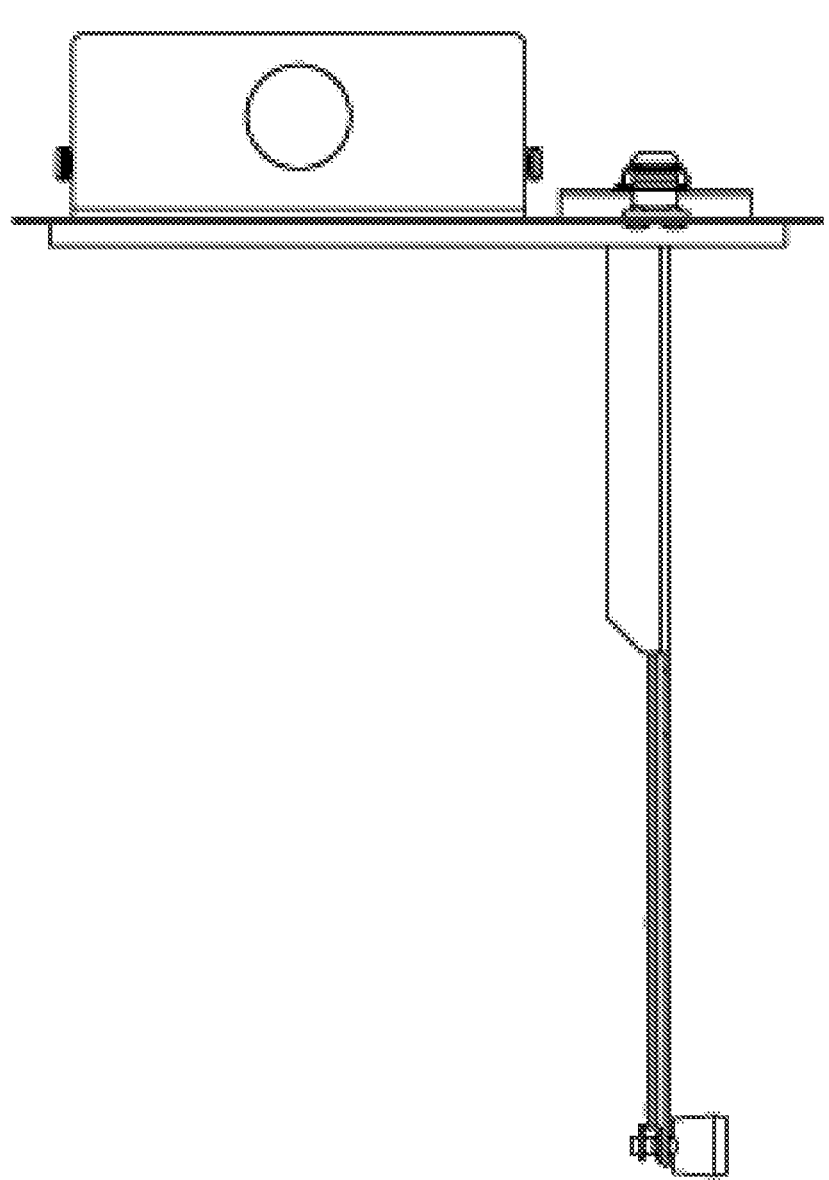
Figure 2E:
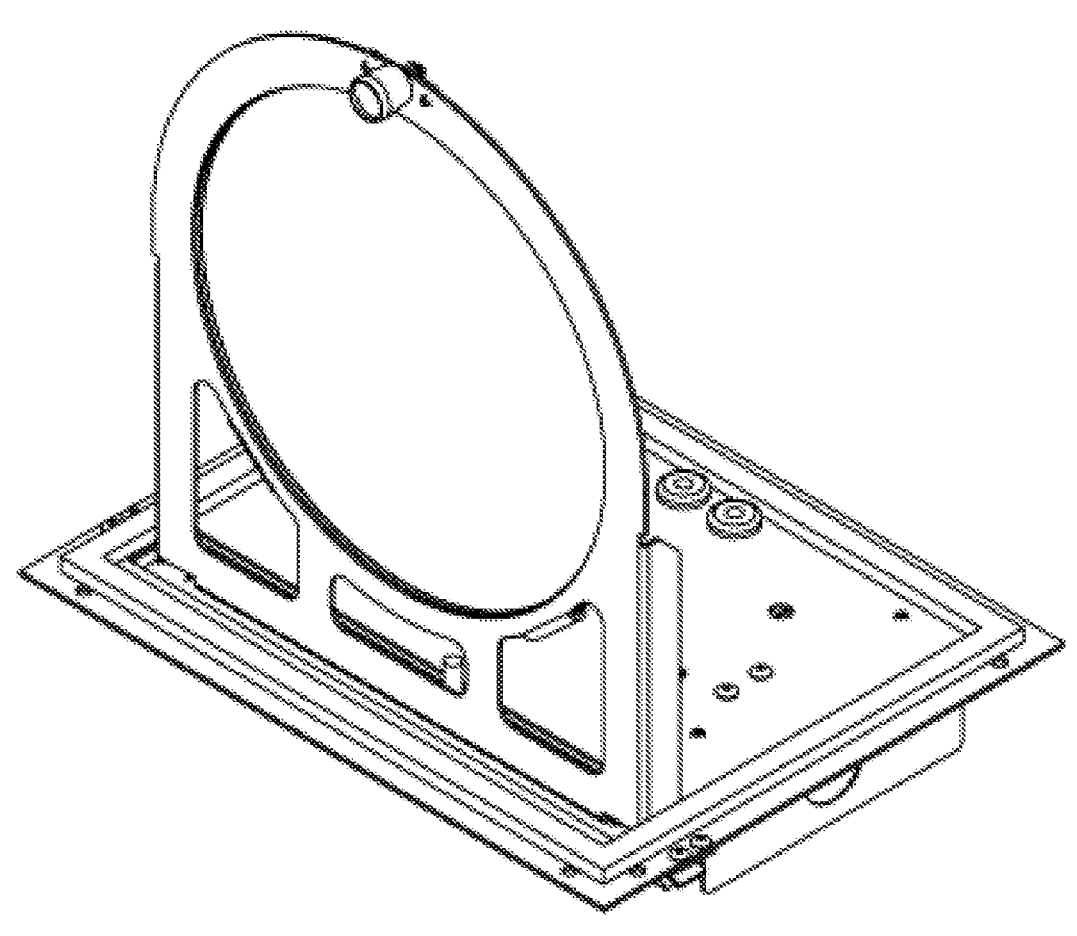

Not to be limited, any combination of mesh substrate, conductive layer, and catalytic layer is suitable for preparing the ECM of the present specification. The active conductive layer and catalytic layers can have adhesive layers or coupling layers separating them without affecting the scope or activity of the ECM.

Corresponding reference characters indicate corresponding parts throughout the several views. The examples set out herein illustrate several embodiments of the present disclosure but should not be construed as limiting the scope of the present disclosure in any manner.

DETAILED DESCRIPTION

Before explaining aspects of the invention in detail, it is to be understood that the invention is not necessarily limited in its application to the details set forth in the following description or exemplified by the Examples. The invention is capable of other aspects or of being practiced or carried out in various ways.

The present disclosure provides for, and includes devices for producing Dry Hydrogen Peroxide (DHP). DHP has been identified as "purified hydrogen peroxide gas" or PHPG. As used herein, DHP is equivalent to PHPG as used in the art. DHP is a non-hydrated gaseous form of $H_2O_2$ that is distinct from liquid forms of hydrogen peroxide, including hydrated aerosols and vaporized forms. DHP is generated in situ from the oxidation of ambient water vapor or through the reduction of oxygen and cannot be produced from a solution of hydrogen peroxide. Aerosolized and vaporized forms of hydrogen peroxide solution have significantly higher concentrations of $H_2O_2$, typically comprising greater than $1 \times 10^6$ molecules per cubic micron compared to air containing DHP that contains between 5 and 25 molecules per cubic micron. Hydrogen peroxide aerosols and vapors are prepared from aqueous solutions of hydrogen peroxide and also differ from DHP as the aerosols are hydrated and, regardless of the size of the droplet, settle under the force of gravity. Vaporized forms condense and settle. Aerosolized forms of hydrogen peroxide are effective antimicrobial agents; however, they are generally considered toxic and wholly unsuitable for use in occupied spaces. See for example, Kahnert et al., "Decontamination with vaporized hydrogen peroxide is effective against *Mycobacterium tuberculosis*," *Lett. Appl. Microbiol.* 40(6):448-52 (2005). The application of vaporized hydrogen peroxide has been limited by concerns of explosive vapors, hazardous reactions, corrosivity, and worker safety. See Agalloco et al., "Overcoming Limitations of Vaporized Hydrogen Peroxide," *Pharmaceutical Technology,* 37(9):1-7 (2013). Further, spaces treated with aerosolized forms, typically at concentrations of between 150 and 700 ppm, remain unsuitable for occupation until the $H_2O_2$ has been reduced by degradation to water and oxygen and the $H_2O_2$. The use of DHP solves the problem of toxicity of aerosolized $H_2O_2$ (e.g., vaporized and liquid forms of $H_2O_2$) and can provide continuous safe antimicrobial and oxidative activity.

DHP is non-hydrated and behaves essentially as an ideal gas. In this form, DHP behaves largely as an ideal gas and is capable of diffusing freely throughout an environment to attain an average concentration of about 25 molecules per cubic micron of air. As a gas, DHP is capable of penetrating most porous materials, essentially diffusing freely to occupy any space that is not airtight. The gaseous form of hydrogen peroxide doesn't settle, deposit, or condense when present at concentrations of at least up to 10 ppm. DHP is completely "green" and leaves no residue as it breaks down the water and oxygen. DHP is formed free of organic species. DHP cannot be prepared from an aqueous solution even if the vaporized form is a so-called "dried" form.

In aspects according to the present disclosure, a device for producing DHP includes an enclosure, an air distribution mechanism, an electrically conductive network having a catalyst on its surface wherein the airflow passes through the electrically conductive network and directs the DHP produced by the device out of the enclosure when the device is in operation. As used herein, an electrically conductive network coated with a catalyst is equivalent to an electro-catalytic mesh (ECM). The conductive network can be directly conductive, such as a copper mesh, or can be indirectly conductive such as a non-conductive material that is coated with a conductive material, for example a polypropylene mesh coated with a metal such as nickel. Also included, and provided for, are ECM having intermediate adhesive layers that covalently bond the electrocatalyst to an electrically conductive substrate. Also including are adhesive layers that bond conductive substrates to non-conductive substrates. The use of conductive layers, catalysis layers, and adhesive layers are well known in the semiconductor industry. As would be evident to a person of skill, a number of the catalysts of the present disclosure are themselves semiconductors (e.g., titanium dioxide, zinc oxide, the titanates).

Previously, it was shown that DHP could be produced by a photocatalytic process using devices having a source of ultraviolet light, a metal or metal oxide photocatalyst (e.g. TiO2), a catalyst substrate structure; and an air distribution mechanism arranged in a morphology that enables the removal of hydrogen peroxide from the reactor before it is reduced back to water. Not to be limited by theory, it is understood that by removing the hydrogen peroxide, the reaction equilibrium of the catalyst is modified so that the photocatalyst preferentially reduces oxygen, rather than hydrogen peroxide, such that it produces hydrogen peroxide from both the oxidation of water and from the reduction of dioxygen. Using morphology that permits immediate removal of hydrogen peroxide gas before it can be reduced, DHP may be generated in any suitable process that simultaneously oxidizes water in gas form and reduces oxygen gas.

Hydrogen ions can be produced electrolytically from water by the following standard reaction:

$$2H_2O \rightarrow 2H^+ + 2e^- + 2OH^* \qquad \text{Oxidation}$$

As hydroxyl radicals build-up they combine to form hydrogen peroxide, which then decomposes into water and oxygen. The oxygen thus produced is then released.

$$4OH^* \rightarrow 2H_2O + O_2 \qquad \text{Oxidation}$$

Hydrogen peroxide gas can be produced electrolytically from ambient oxygen and osmotically supplied hydrogen ions using the following reaction:

$$O_2 + 2H^+ + 2e^- \rightarrow H_2O_2 \qquad \text{Reduction}$$

In the context of the present disclosure, DHP may be produced using an electrolytic process with a purpose-designed morphology that enables the removal of near-ideal gas phase hydrogen peroxide from the reactor before it is forced to undergo subsequent reduction or oxidation. Without intending to be limited, in operation, hydrogen peroxide gas may be produced at a greatly accelerated rate compared to photocatalytic methods. Not to be limited by theory, it is thought that the electrolytic process is not subject to limitations caused by low humidity, by the comparatively slow rate at which humidity is absorbed onto the photocatalyst, or by airborne contaminants such as nitrogen oxides that interfere with the photocatalytic reaction. Additionally, by controlling the electrical potential, or voltage, applied, the rate of production of near-ideal hydrogen peroxide gas can be readily regulated or optimized for use in a given space or application, and controlled to provide concentrations down to the limits of detection (e.g., about 1 ppb) or as high as seven or more parts per million. However, without being limited by theory, it should be noted that the intended uses and methods of use of the devices of the invention are not achieved as a result of the electrolytic process, but by the effects of near ideal gas hydrogen peroxide (e.g., DHP) once it is released into the environment.

Using morphology that permits immediate removal of hydrogen peroxide gas before it can be reduced, near-ideal gas hydrogen peroxide may be generated in any suitable manner known in the art, including but not limited to, any suitable process known in the art that simultaneously oxidizes water (or another compound that can provide hydrogen ions separable by osmosis) in liquid or gas form, and reduces oxygen gas, including gas phase photo-catalysis, e.g., using a metal catalyst such as titanium dioxide, zirconium oxide, titanium dioxide doped with co-catalysts (such as copper, rhodium, silver, platinum, gold, etc.), or other suitable metal oxide photocatalysts. Near-ideal gas hydrogen peroxide may also be produced by electrolytic processes using anodes and cathodes made from any suitable metal, or constructed from metal oxide ceramics using morphology that permits immediate removal of hydrogen peroxide gas before it can be reduced.

Continuously produced via a hydrogen peroxide diffuser device, as discussed herein, an equilibrium concentration above 0.04 parts per million of near-ideal gas phase hydrogen peroxide may be achieved and maintained continuously in an environment. At equilibrium at one atmosphere pressure and 19.51 degrees Celsius, near-ideal gas phase hydrogen peroxide will be present in every cubic micron of air at an average amount of one molecule per cubic micron for each 0.04 parts per million of concentration. At one part per million, the average number of hydrogen peroxide molecules per cubic micron will be 25, and at seven parts per million it will be 175. As used herein, DHP comprises gaseous hydrogen peroxide ($H_2O_2$) that is substantially free of hydration, ozone, plasma species, or organic species.

As used herein, the term "free of ozone" means an amount of ozone below about 0.015 ppm ozone. In an aspect, "free of ozone" means that the amount of ozone produced by the device is below or near the level of detection (LOD) using conventional detection means. Ozone detectors are known in the art and have detection thresholds in the parts per billion using point ionization detection. A suitable ozone detector is the Honeywell Analytics Midas® gas detector capable of detecting 0.036 to 0.7 ppm ozone.

As used herein, "free of hydration" means that the hydrogen peroxide gas is at least 99% free of water molecules bonded by electrostatic attraction and London Forces. Hydrated forms of hydrogen peroxide are produced by evaporation and atomization of aqueous hydrogen peroxide (AHP). Aerosols and vapors produced from AHP are a hydrated form of hydrogen peroxide having each molecule surrounded by shell of water molecules (hydration shell) bonded by electrostatic attraction and London Forces. While there are various "drying" methods, such methods cannot remove the hydration shell.

Also as used herein, a DHP that is free of plasma species means hydrogen peroxide gas that is at least 99% free of hydroxide ion, hydroxide radical, hydronium ion, hydrogen radical, and combinations thereof.

The present specification reports the production of DHP using a new, electrolytic process. The fundamental nature of an electrolytic process is to create a flow of electrons from one set of chemical reactants to another, thereby inducing paired oxidation and reduction reactions to produce products. This occurs when an electrical potential, or voltage, is supplied between two electrodes, each of which is exposed to reactants. The reaction can be controlled by optimizing the voltage to provide products at the desired rate, modifying the catalytic substrate (e.g., selecting catalyst, co-catalyst, additive), modifying the conductive network, and adjusting the air flow, including adjusting the humidity.

The present disclosure provides for devices that provide for the production of DHP using the electrolytic process comprising an electrically conductive network coated with a catalyst and powered by an electrical power source. The device can be installed into a separate enclosure comprising an air distribution mechanism or installed into an HVAC system that provides for an air distribution mechanism.

As used herein, an "electrically conductive network" refers to a meshwork, a fabric, an extruded catalyst, or structure that is electrically conductive. As used herein, an air-permeable electrically conductive network refers to a meshwork or a fabric. As used herein, unless indicated otherwise explicitly or clearly indicated by the context, the terms "electrically conductive network", "air-permeable electrically conductive network", "conductive network", and "network" may be used interchangeably. The electrically conductive networks of the present disclosure when coated by a catalyst are also referred to as a "sail." Previous photocatalytic devices included similar air permeable substrate structure (e.g., meshes) coated with a catalyst (e.g., "sails") except that the substrate is non-conductive. Thus, it would be evident that certain $TiO_2$ catalyst coated conductive sails of the present disclosure could be incorporated in prior art devices (e.g., as described in International Patent Publication No. WO 2015/171633 and the '617 Publication). However, the earlier sails are not compatible with the present disclosure which requires a conductive substrate structure.

Figure 6:
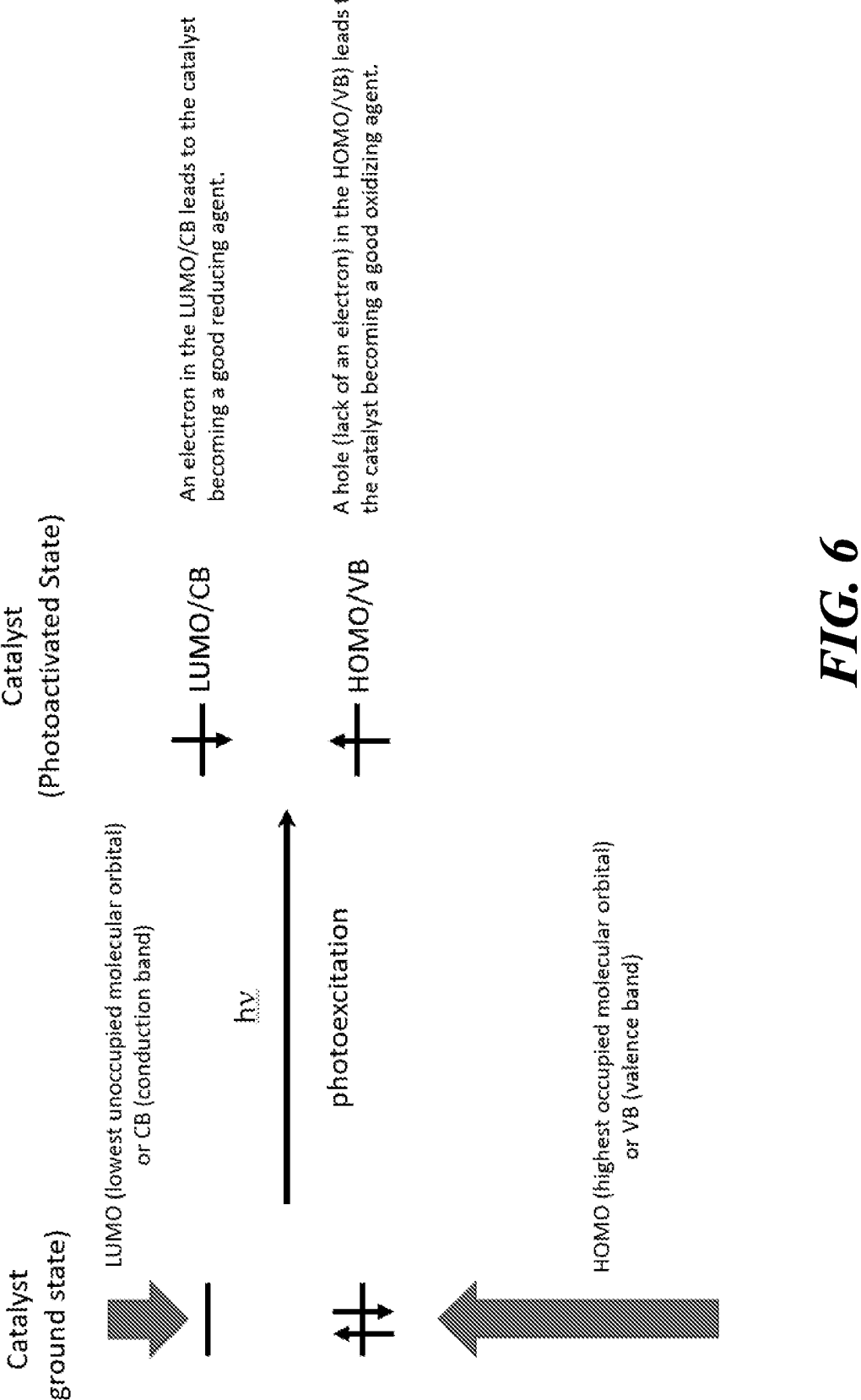
FIG. 6 is a diagram of the energy states during photocatalytic activation of a catalyst. Absorption of a photon of sufficient energy excites an into the lowest unoccupied molecular orbital (LUMO or conduction band CB) in the catalysts to create a reducing agent. The unpaired electron, or hole, remaining in the highest occupied molecular orbital (HOMO or valence band (VB)) results in the catalyst becoming a good oxidizing agent.

Photocatalytic DHP production is unique in that it permits both oxidation and reduction half reactions to occur on the catalyst within close proximity to each other. See FIG. 6. By example, when Titanium Dioxide ($TiO_2$) is used as the catalyst, it behaves as a semiconductor. At rest, it operates as an insulator, with no usable electrical activity. When stimulated with sufficiently energetic light of 435 nm or lower wavelengths, however, electrons within the $TiO_2$ are promoted from valence band energy levels, across the band gap, into conduction band (CB) energy levels (lowest unoccupied molecular orbital (LUMO)), thus becoming a free electron ($e^-$). The electron in the LUMO/CB leads to the catalyst being a good reducing agent. Correspondingly, a vacancy, an electron hole ($h^+$) is formed in the vacated valence band (VB or highest occupied molecular orbital (HOMO)) leading to the catalyst becoming a good oxidizing agent. This reaction is represented by the following equation:

$$\text{Photon } (hv) \rightarrow e^- + h^+.$$

Once the free electron and the electron hole have been produced, oxidation reactions are initiated by the electron holes, and reduction reactions are initiated by the free electrons. The limitation of this process is that free electrons and electron holes recombine within microseconds (releasing wasted heat) unless adsorbed species are present to react with them. This means that the efficiency of the photocatalytic process is severely limited by the rate of adsorption of reactive species onto the surface of the catalyst, and the corresponding presence of either an electron hole or a free electron with which to react. When they occur, these reaction sequences are:

$$2h^+ + 2H_2O(\text{humidity}) \rightarrow 2OH^*(\text{hydroxyl radicals}) + \quad \text{Oxidation:}$$
$$2H^+ \text{ (hydrogen ions)} 2OH^* \rightarrow H_2O_2(\text{DHP})$$

$$2e^- + 2H^+ + O_2(\text{oxygen}) \rightarrow H_2O_2(\text{DHP}) \quad \text{Reduction:}$$

To prevent the hydroxyl radicals from simply combining with the free electrons and hydrogen ions to produce humidity, the thermodynamically favored reaction, an airflow is applied that is strong enough to separate the hydroxyl radicals from the catalyst surface, yet insufficiently strong enough to overcome the electrostatic attraction between the free electrons, or the hydrogen ions and the catalyst surface. Isolated from the free electrons and the hydrogen ions, the hydroxyl radicals then react with each other to form DHP.

Figure 7:
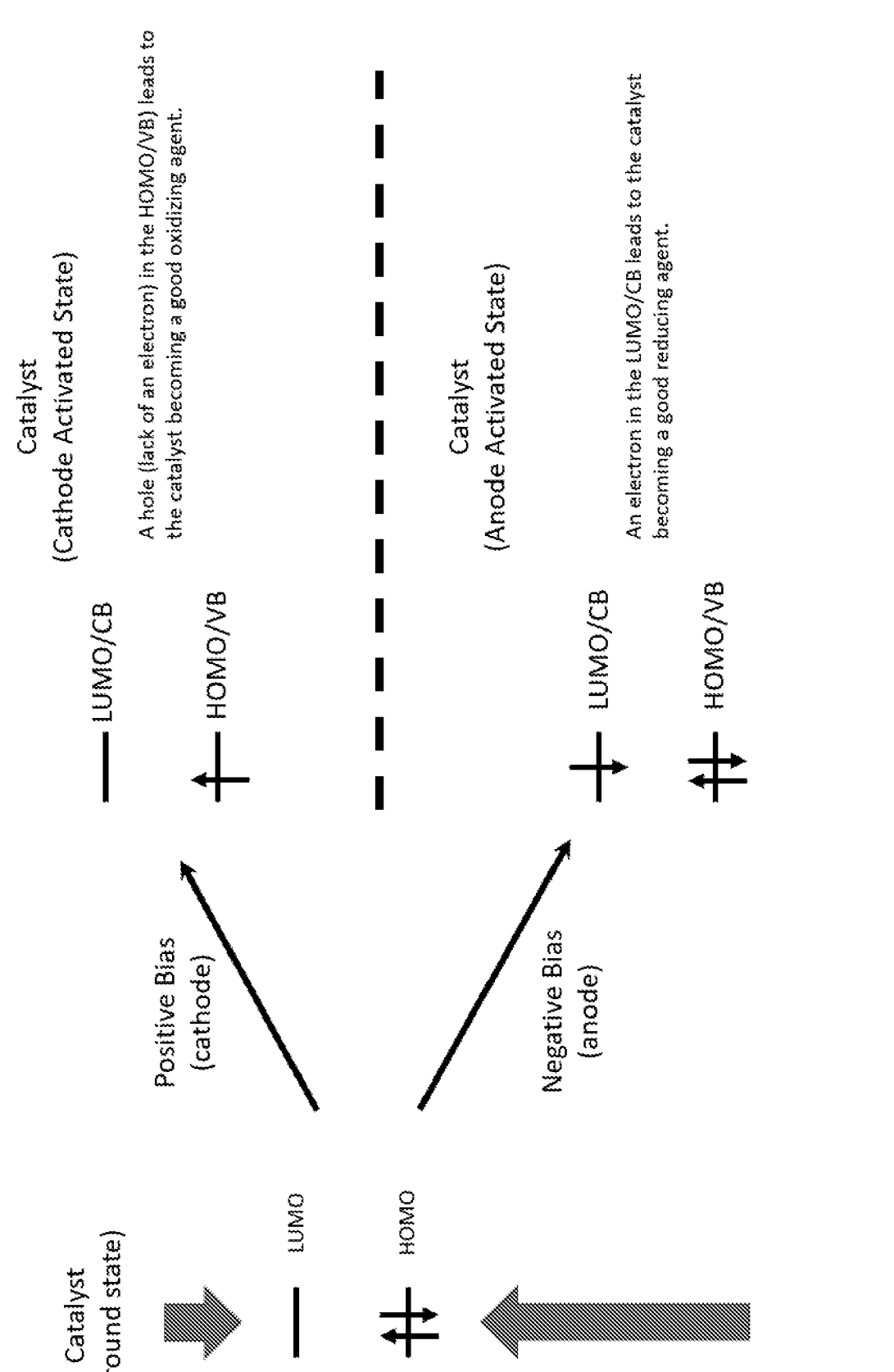
FIG. 7 is a diagram of the energy states during electrocatalytic activation of a catalyst in an aspect of the present specification. On the positive cathode, withdrawal of an electron from the HOMO/VB results in an electron hole and formation of a good oxidizing agent. At the anode, the catalyst is activated by a free electron that occupies the LUMO/CB to produce a good reducing agent.
Figure 8A:
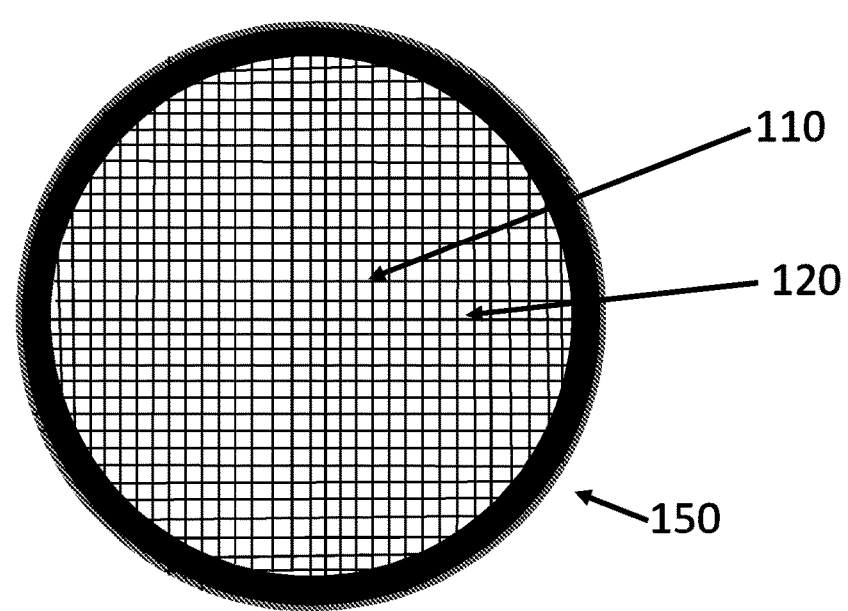
FIGS. 8A and 8B illustrates an electrocatalytic mesh (ECM) 100 according to an embodiment of the present disclosure.
Figure 8B:
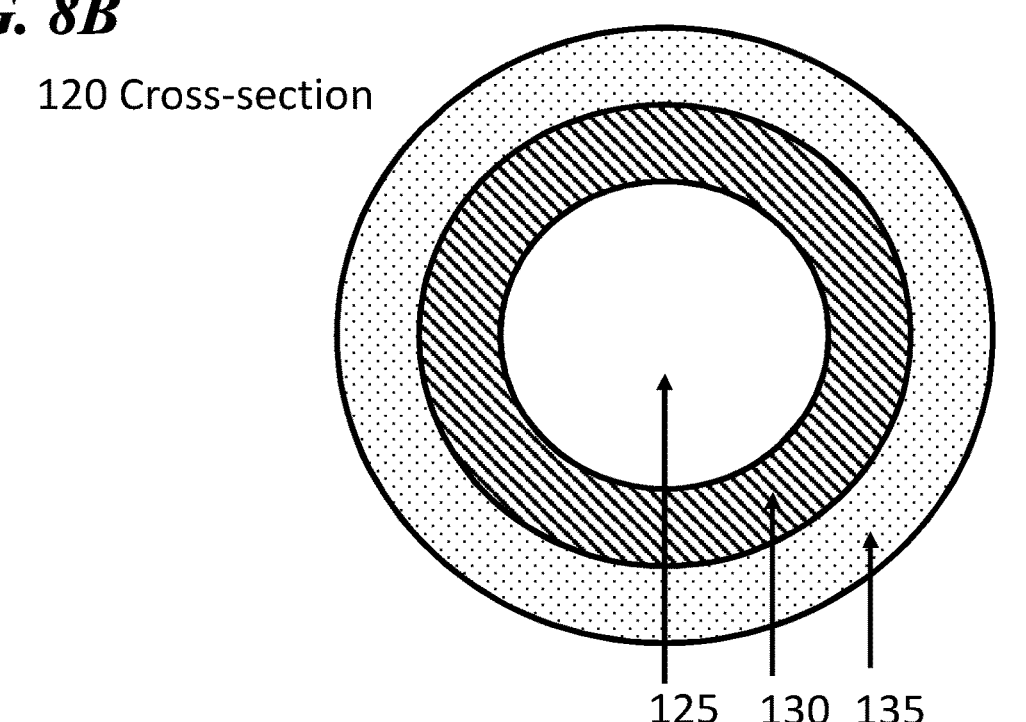
Figure 10:
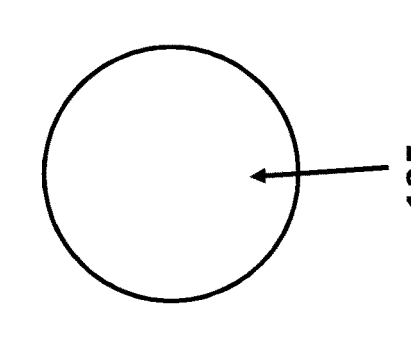
FIG. 10 illustrates the preparation of the ECM according to an aspect of the present disclosure. Conductive layer 125 is first coated with an adhesive layer 130 and the electrocatalyst layer 135 is deposited.
Figure 10:
Figure 10:
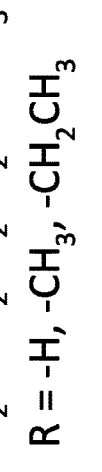
Figure 11:
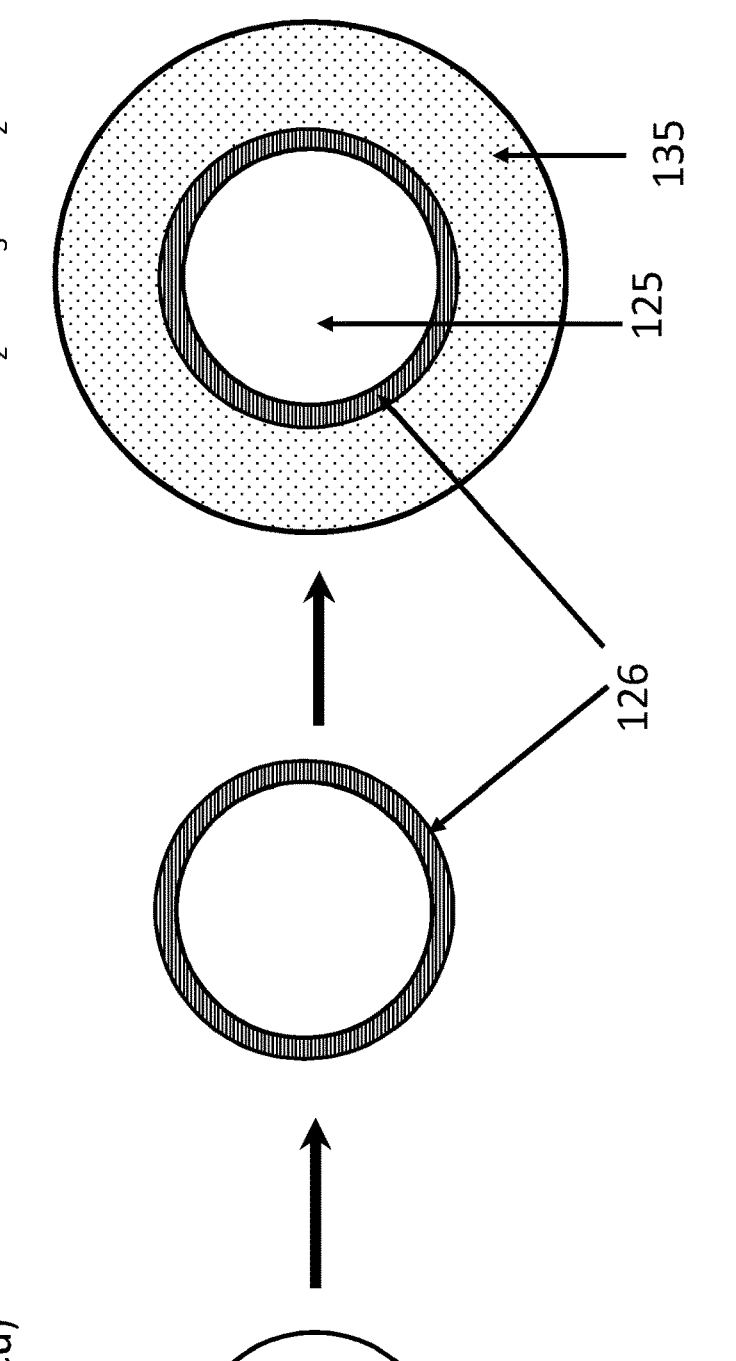
FIG. 11 illustrates the preparation of an ECM according to an aspect of the present disclosure. Conductive layer 125, such as silver (Ag) or copper (Cu) is coated with a second, conductive layer 126, for example, nickel (Ni) or chromium (Cr) deposited by electroplating (e.g., Ni, Cr) or electroless plating (Ni). The electrocatalyst 135 is then deposited on the conductive layer 126.
Figure 12:
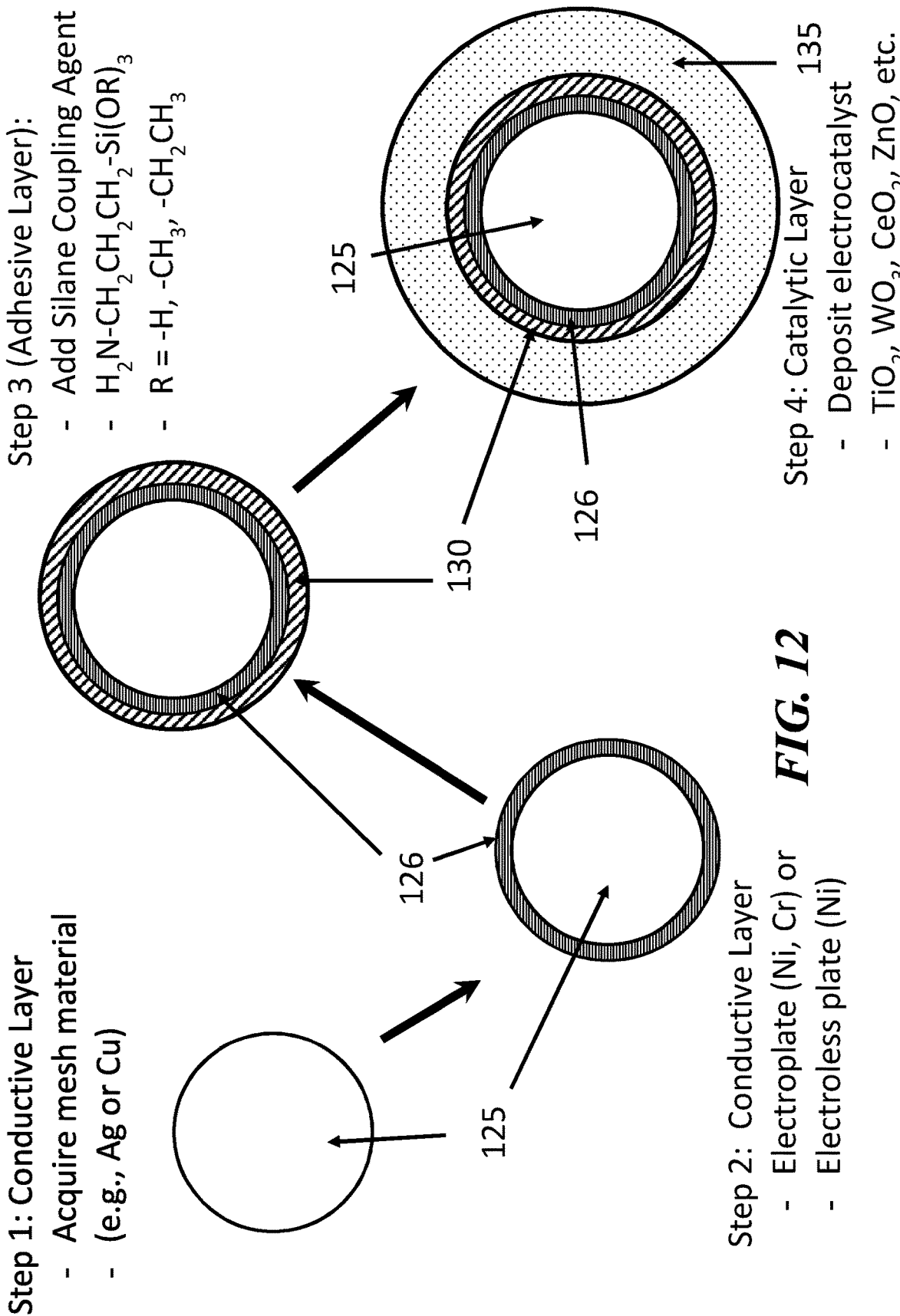
FIG. 12 illustrates the preparation of an ECM according to an aspect of the present disclosure. Conductive layer 125, such as silver (Ag) or copper (Cu) is coated with a second, conductive layer 126 as shown in FIG. 11 and then further coated with an adhesive or coupling layer comprising, for example a silane coupling agent (SCA). The electrocatalyst 135 is then deposited and covalently bonded to the SCA
Figure 13:
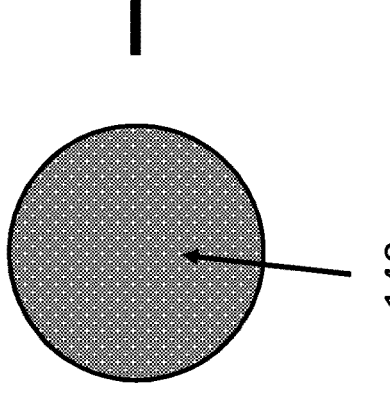
FIG. 13 illustrates the preparation of an ECM starting from mesh prepared from a non-conductive base material 140. The base material 140 is coated by electroless plating to provide a conductive layer 125. Conductive layer 125 is in turn coated with a catalytic layer 135.
Figure 14:
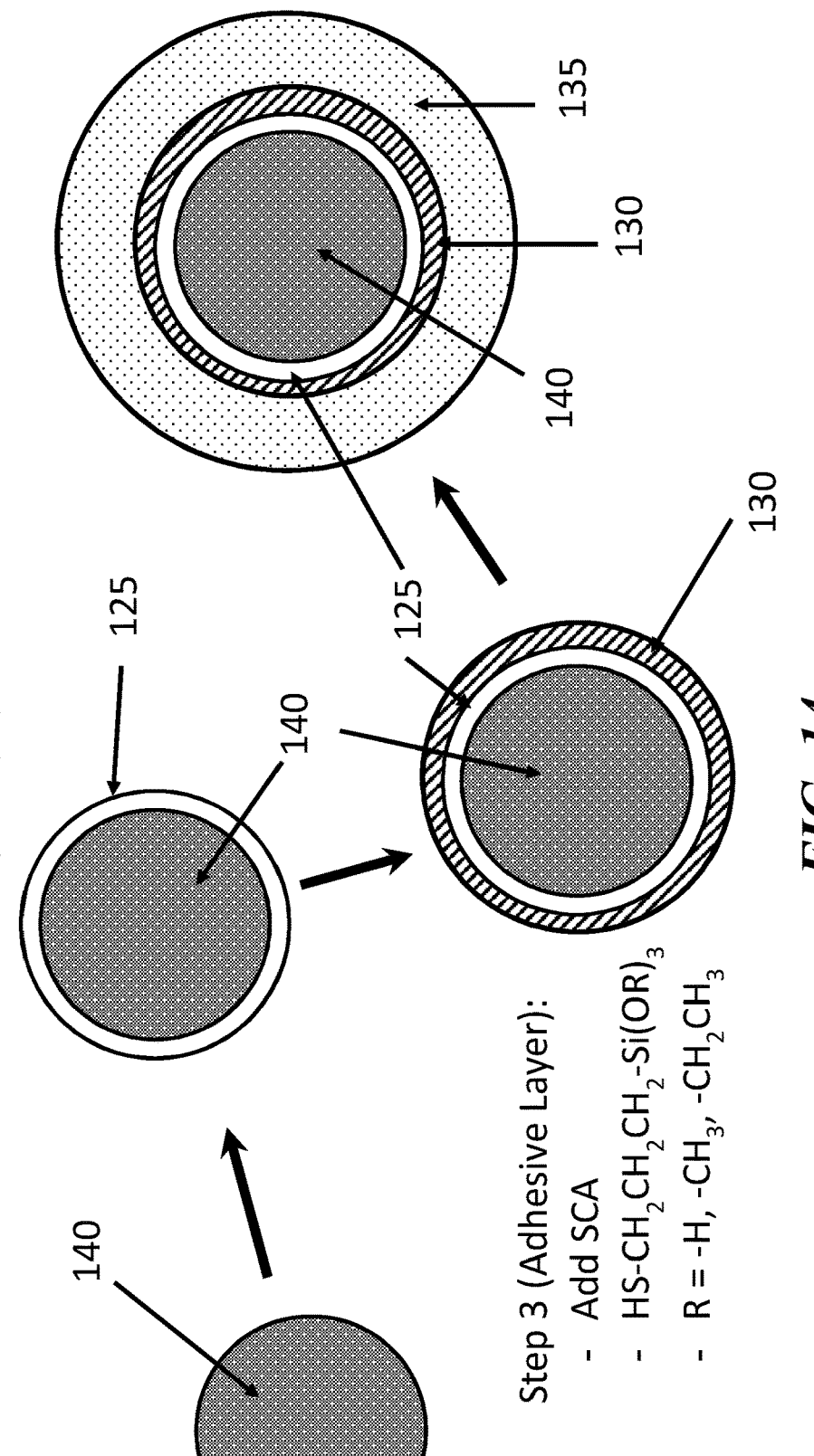
FIG. 14 illustrates the preparation of an ECM starting from a mesh prepared from a non-conductive base material 140 as provided in FIG. 13. The base material 140 is first coated with a conductive layer 125 and then further coated with an intermediate adhesive or coupling layer 130. The coupling layer 130 then provides for the deposition and coupling of the catalytic layer 135.
Figure 15:
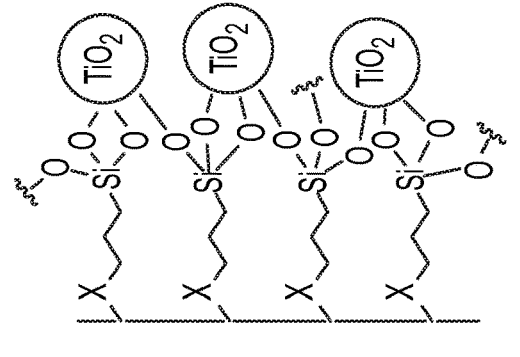
FIG. 15 illustrates the adhesive chemistry of amino- or thio-silanes and the coupling of catalytic substrates to conductive metal surfaces. As shown in A, amino silanes form covalent bonds with the metal surfaces of silver and copper. As shown in B, thio-silanes form covalent bonds with stainless steel and nickel. The siloxyl group covalently bonds with the catalyst, shown in FIGS. 15A and 15B as titanium dioxide.
Figure 15:
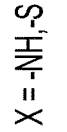
Figure 15:
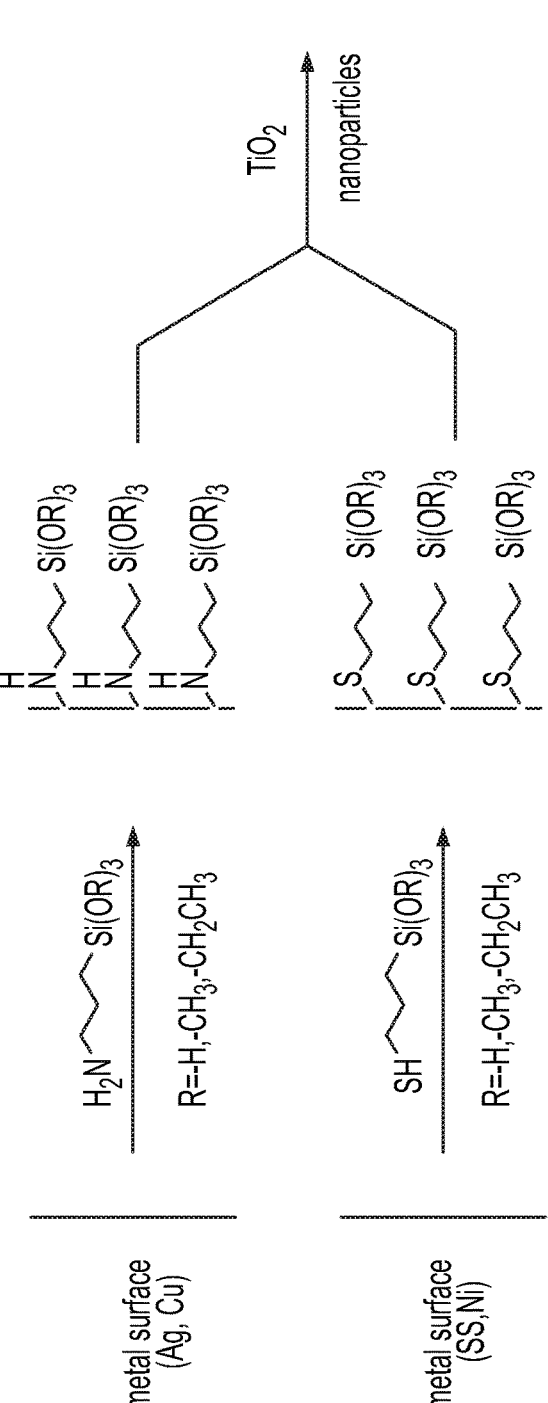
Figure 15:
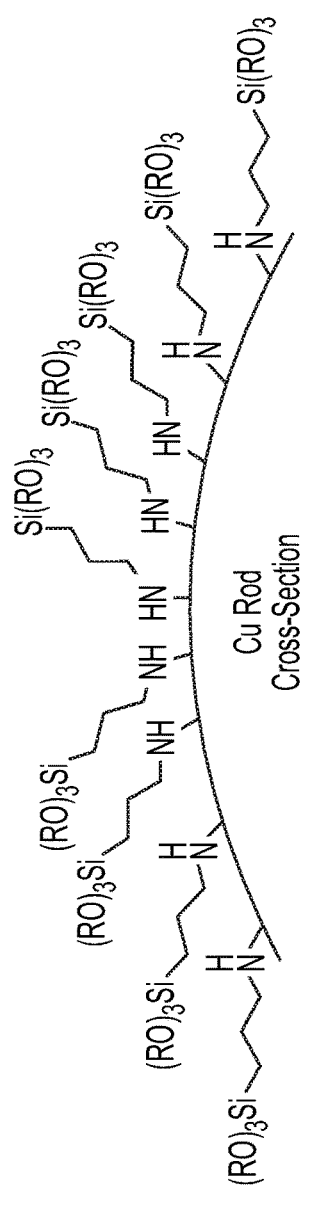

By contrast, an electrocatalytic surface cannot readily perform both oxidation and reduction reactions in close proximity to each other. At any given moment in time, the electrocatalytic surface must act as either a cathode, facilitating oxidation reactions, or as an anode, facilitating reduction reactions. See FIG. 7.

Not to be limited by theory, it is understood that when the electrocatalytic surface acts as a cathode, electrons are drawn from the catalyst by an applied current, creating electron holes in the HOMO/VB in the absence of free electrons (eliminating inefficiencies associated with free electron/electron hole recombination to produce wasted heat). Under this condition, adsorbed water molecules are oxidized by the electron holes into hydroxyl radicals and hydrogen ions. Then the hydroxyl radicals are separated from the electrocatalytic surface by the above-mentioned airflow, to form DHP. The hydrogen ions remain on the photocatalytic surface, and as they build up the thermodynamic activation energy required to oxidize each successive water molecule increases, requiring progressively more voltage.

Since hydrogen ions are required to produce DHP by the reduction of oxygen, action of the electrocatalyst as an anode can only occur after a sufficient period of cathodic activity and associated hydrogen ion buildup. Not to be limited by theory, when operating as an anode, conducting free electrons are supplied to the catalyst by an applied current, at which point they react with adsorbed oxygen molecules and hydrogen ions as shown above to produce DHP, which is then separated from the catalyst by air flow. This is expected to occur until all of the accumulated hydrogen ions are consumed, at which point the system must shift back into operation as a cathode.

Electrocatalytic DHP production is surprisingly efficient compared to photocatalytic DHP production. Initial experiments with less than a 5% coating of titanium dioxide on a copper metal substrate yielded DHP levels within the same range as a photocatalytic DHP generator set to provide 20 ppb to 40 ppb of DHP. Not to be limited by theory, this gain in efficiency is thought to be the product of two effects. First, the electrocatalytic system provides continuous creation of either electron holes or free electrons without loss of efficiency due to the haphazard recombination of free electrons with electron holes to produce wasted heat. As humidity (water molecules) or oxygen molecules adsorb onto the catalyst, they can react respectively, without delay, with either electron holes or free electrons to produce DHP. Second, it is theorized that the most rate limiting factor of photocatalysis, the rate of adsorption of water molecules onto the catalyst, is greatly enhanced because of much stronger electrostatic attraction between polar water molecules and the constantly available positively charged electron holes. The presence of a constant and plentiful supply of electron holes actually increase the rate of water adsorption onto the catalyst, and thus, the rate of reaction.

The impact of electrocatalytic DHP production is immense. With the production of DHP freed from the photocatalytic requirement of a light source and the maintenance of that light source, design is no longer restricted by size of the light source or the need to periodically replace it. Efficiency losses from the air conditioned cooling of fluorescent bulbs, or the warming of light emitting diodes by heating systems, are also eliminated. Further, because of the greatly increased efficiency of electrocatalysts, devices can be made even smaller, using respectively smaller and quieter fans. Energy requirements will also decrease markedly.

Photocatalytic sails require illumination, most efficiently direct illumination, and in theory are limited to the total cross-sectional surface area that is illuminated. Further, increases in the intensity or amount of light have limited benefit as DHP is photolyzable. Thus, as light increases it can begin to break down the DHP thus reducing device efficiency. The electrocatalytic system of the present disclosure is not similarly limited and provides a significant advantage to photocatalytic systems.

While results demonstrate that ECM sails are more efficient than photocatalytic sails, not to be limited by theory, there appear to be limitations to DHP production. DHP concentrations maybe self-regulating due to the electrostatic attraction between DHP molecules which degrade to water and oxygen upon reacting with each other. DHP self-regulation occurs whenever the concentration of DHP results in intermolecular spacing that is closer in distance than the electrostatic attraction range of the DHP molecules. When this occurs, DHP molecules are attracted to, and degrade each other until the concentration drops sufficiently that the intermolecular spacing is greater than the electrostatic attraction range of the DHP molecules.

Second, the photocatalytic and ECM sails will have reactive plasmas on their surfaces and the majority of the chemical species in the electrocatalytic plasma are reactive with hydrogen peroxide. Plasma components, particularly hydroxyl radicals inhibit the overall production of hydrogen peroxide gas by means of reactions that destroy hydrogen peroxide. Thus, DHP containing air, when passed through a device is not expected to increase the overall concentration. Thus, in practice, the total amount of DHP is more limited than what can currently be achieved using either photocatalytic or ECM based processes.

With regard to applications, a much broader field of venues and operational approaches are also possible. Electrocatalytic DHP devices can be deployed in smaller places, arrayed more efficiently for larger spaces, distributed more easily to provide multiple small point sources throughout a space, can operate at lower ambient temperatures, can operate at higher ambient temperatures, and can operate in more arid environments, as low as 1% relative humidity due to more efficient water adsorption compared to the current operational lower limit of 20% relative humidity.

Direct current (DC) is one means by which to produce DHP electrocatalytically, though it is understood to be less efficient. Not to be limited by theory, using direct current the catalyst first operates as a cathode, as expected, until the thermodynamic activation energy caused by the buildup of hydrogen ions on the catalyst reaches a critical point that has not been fully characterized. At this point, it is thought that the electrocatalyst force-shifts to operation as an anode until the hydrogen ions are consumed. Initial experiments with a copper metal substrate bearing less than a 5% coating of titanium dioxide exhibited a subsequent pause before the electrocatalyst shifted back into cathodic operation, but this pause was progressively reduced as the amount of coating was increased.

The present specification provides for and includes, electrocatalytic devices employing an Alternating Current (AC) electrical power source. An electrocatalytic device having an AC power source is expected to be more efficient than direct current, but rapid, sudden, analog shifts from cathodic to anodic state under standard utility cycles such as 60 cycles per second, or 60 Hertz, are not expected to establish a semi-steady state long enough to optimize DHP production using the sails of the present specification.

The present specification provides for and includes, electrocatalytic devices employing an a Modulated Alternated Current ("MAC") electrical power source. It is expected that a MAC powered electrocatalytic device provides the best optimization. Modulated current is defined as a sinusoidal DHP production cycle, where the electrocatalyst is initiated by cathodic operation at a nominal current and voltage, then over the course of seconds the current and voltage are reduced to zero, the electrocatalyst is shifted to anodic DHP production as current and voltage are increased, and then decreased again to shift back into cathodic DHP production as the cycle is repeated.

As noted above, each substrate has its own substance-unique resistance that must be taken into account in the selection of the electrically conductive network. The lower the resistance, the more efficient the electrically conductive network will be. The catalyst itself has a resistance associated with its band gap. The most efficient, but not necessarily the optimal, catalyst for a system that can oxidize water to hydroxyl radicals is the one whose band gap is closest in energy to the energy required to produce a hydroxyl radical (2.85 eV). During operation, the production and accumulation of hydrogen ions on the catalyst increases the thermodynamic resistance and the voltage required for electrocatalysis. Accordingly, a catalyst with a larger band gap/ greater resistance (for example titanium dioxide) may remain optimal because it provides a longer oxidation cycle before a force shift occurs.

The present disclosure provides for, and includes, conductive networks that comprise a metal meshwork ("metal mesh"). In an aspect, the metal mesh comprises a metal selected from the group consisting of copper, annealed copper, silver, gold, aluminum, tungsten, zinc, nickel, iron, platinum, tin, titanium, grain oriented electrical steel, stainless steel, and nichrome. Any conductive metal having a conductivity ($\sigma$) between $6.3 \times 10^7$ Siemens per meter (S/m) and $1 \times 10^5$ S/m at 20° C. are suitable for preparing a meshwork and coating with the catalysts of the present disclosure to prepare a sail for the electrolytic production of DHP. Similarly, any suitable metal having a resistivity (p) between $1.5 \times 10^{-8}$ ohm-meter ($\Omega \cdot$m) and $3 \times 10^{-3}$ ohm-meter ($\Omega \cdot$m) at 20° C. are suitable for preparing a meshwork and coating with the catalysts of the present disclosure to prepare a sail for the electrolytic production of DHP. As provided herein, the metal meshes have a percentage of open area of between 20% and 60% after coating with a catalyst (see below for additional details).

The present disclosure further provides for, and includes, conductive networks are organic conductive materials. To become effective, organic conductive materials (which are intrinsically non-active) are oxidatively doped—making them ideal materials for the generation of DHP. The materials are exposed to oxidative conditions to improve their conductivity from $<10^{-8}$ S/cm to $>0.1$ S/cm. Suitable organic conductive materials include polyacetylene, PPV (polyphenylene vinylene), polypyrrole, polythiophene, or polyphenylene sulfide. In an aspect, the organic conductive material is polyacetylene. In an aspect, the organic conductive material is a polythiophene such as PEDOT:PSS mixture (poly(3,4-ethylenedioxythiophene-poly(styrene-sulfonate)) as provided by Millipore-Sigma (St. Louis, Mo.).

In aspects included and provided by the present specification, ECM sails can be prepared on non-conductive support materials and then coated with a conductive coating. In an aspect, the conductive coating can be applied directly to the support material or indirectly using an adhesive. See FIG. 6. The now-conductive support material can be coated, again either directly or indirectly, with a catalyst and used to prepare an ECM sail. By using strong conductive fabrics or meshes ECM sails can be prepared from natural fibers such as cotton, wool, or cellulose. In aspects, rigid ECM sails are prepared that can support the air speeds produced by the fans blowing air across the 'sail' to 'push' water-containing air through the electrocatalytic sites that are being supported by these materials. Thinner metallic conductive coatings may then be used—lowering the cost and weight of the 'sails.' Alternatively, flexible support materials may be used, and the material 'stretched' between a frame allowing the air blow across the sail.

The present disclosure further provides for, and includes, the use of conductive fabrics for the electrically conductive network. In some aspects, the conductive fabric is a metal coated fabric comprising nylon, polyester coated with a metal selected from the group consisting of copper, annealed copper, silver, gold, aluminum, tungsten, zinc, nickel, iron, platinum, tin, titanium, grain oriented electrical steel, stainless steel, and nichrome. In other aspects, the conductive fabric may incorporate the conductive material (usually metal) into the fiber. Such conductive fibers can then be woven in to fabrics of any type, incorporating the meshes as described below. Fabrics suitable for coating with a catalyst and using in the devices of the present disclosure are available for example from Less EMF Inc. (Latham NY). Suitable conductive fabrics include, but are not limited to, silver coated nylon fabrics (CIRCUITeX™, Cat. #A325), nickel/copper/cobalt plated polyester (COBALTEX™, Cat. #A1271), nickel/copper plated polyester (Nickel/Copper Ripstop Fabric, Cat. #A1213), polyester mesh comprising copper and silver filament containing yarn (DAYLITE™, Cat. #A332), and stainless steel wire knitted with 40% polyester yarn (ESD Static Fabric, Cat. #A1272). Other conductive fabrics having an electrical resistivity of between $1.5 \times 10^{-8}$ ohm-meter ($\Omega \cdot$m) and 5 ohm-meter ($\Omega \cdot$m) at 20° C. are suitable to be coated with a catalyst to prepare a sail for the electrolytic production of DHP. As provided herein, the conductive fabric has a percentage of open area of between 20% and 60% after coating with a catalysts (see below for additional details).

The devices of the present disclosure include an electrically conductive network having a catalyst on the surface configured to produce dry hydrogen peroxide gas when applied to a current carrying electrically conductive network and provided an airflow. Not to be limited by theory, it is thought that hydrogen peroxide gas generated on the catalyst surface is released from the surface and thereby prevented from being reduced back into water by the catalyst or hydroxide.

The present disclosure also provides for electrically conductive networks that are coated with a catalyst. In some aspects, a network may comprise a material that is coated with one or more catalysts. In other aspects, a network may comprise a material that is coated with a catalyst and one or more co-catalysts. In yet another aspect, a network may comprise a material that is coated with a mixture of a catalyst, co-catalyst, and an additive.

A variety of methods for coating an electrically conductive network are currently known. In certain aspects, an electrically conductive network is coated with a crystalline titanium dioxide powder in one or more applications and sintered in an oven. The coatings of the present disclosure may be applied to a conductive network by a variety of methods including, but not limited to, gel sol methods, painting, dipping, and powder coating. In other aspects, the catalysts, co-catalysts and additives of the present disclosure may be applied to a conductive network by toll coating, tape casting, ultrasonic spray, and web-based coating. As provided herein, the method of applying the catalysts, co-catalysts, and additives is suitable if it provides for, and includes, retaining the conductive network of the underlying electrically conductive network as recited above.

The present disclosure also provides for the use of adhesive layers 130 to join catalyst materials 135 to conductive meshes 125. In aspects, adhesives 130 are also used to adhere conductive materials 125 to non-conductive support materials 140.

In aspects of the present disclosure, adhesive layers are selected to join metal oxides to conductive inorganic materials. A variety of suitable materials are known including silane coupling agents (SCAs). SCAs coordinate to the surface of the conductive layer via an amine or thiol group leaving the siloxy portion of the molecule sticking out of the surface. The metal oxides are then adhered to the siloxy portion. In an aspect, the SCA is selected from the group consisting of 3-mercaptopropane trimethoxysilane, 3-mercaptopropane triethoxysilane, 3-mercaptopropane silane-triol, 3-aminopropane trimethoxysilane, 3-aminopropane triethoxysilane, and 3-aminopropane silane-triol. In an aspect, the SCA is 3-mercaptopropane trimethoxysilane. In another aspect, the SCA is 3-mercaptopropane triethoxysilane. In a further aspect, the SCA is 3-mercaptopropane silane-triol. In yet another aspect, the SCA, 3-aminopropane trimethoxysilane. In an aspect, the SCA is 3-aminopropane triethoxysilane. In yet a further aspect, the SCA is 3-aminopropane silane-triol.

When using conductive metals such as Ag and/or Cu, the amino-terminated SCA gives stronger bonding interactions (Ag—NH$_2$R, Cu—NH$_2$R), whereas with Ni, stainless steel, the thiol-terminated SCA gives stronger bonding interactions (Ni—SR, stainless steel-SR). An example of this technique would be to react the Ag or Cu mesh network with 3-aminopropyl trimethoxysilane to provide a coated surface where the amine was directly attached to the surface of the metal—leaving the siloxane exposed for electrocatalyst deposition. The —Si(OR$_3$) (R═—H, —CH$_3$ or CH$_2$CH$_3$) then reacts with the TiO$_2$ (or other electrocatalyst) to form covalent bonds to the electrocatalyst—increasing the adhesion to the metallic surface. This is described in the Gelest (Morrisville, Pa.) publication, "Silane Coupling Agents: Connecting Across Boundaries", 3$^{rd}$ Ed., B. Arkles (which can be downloaded from the internet at www(dot)gelest(dot) com/wp-content/uploads/Goods-PDF-brochures-couplin-gagents.pdf).

Furthermore, for increased stability, either electroplating Ag or Cu conductive mesh networks with a Ni-based solution or Cr-based solution (see "Nickel Plating Handbook" 2014 from the Nickel Institute), or using an electroless deposition of Ni onto the surface of Ag or Cu conductive mesh networks (as supplied by Coating Technologies (Phoenix, Ariz.) or Metal Chem., Greer, S. C.)—a layer having better adhesion for the electrocatalyst is obtained. Additionally, any electromobility of Cu$^{2+}$ or Ag$^+$ ions (obtained through oxidation of the metal mesh network) is eliminated by incorporating these layers directly on the conductive trace surface. Furthermore, as an optional layer—the SCA layer using the 3-mercaptosiloxane (HS—CH$_2$CH$_2$CH$_2$Si (OR)$_3$, where R═—H, —CH$_3$, —CH$_2$CH$_3$) may also be used on the resulting electroplated or electroless plated layers to also increase adhesion after the electromobility issue has been solved with the Ni or Cr plating.

In aspects of the present disclosure, adhesive layers are selected to join metal oxides to conductive organic materials. Types of suitable adhesive materials include vinyl triethoxysilane (or vinyl trimethoxysilane or vinyl silane-triol), C$_6$ through C$_{24}$ trimethoxysilane, C$_6$ to C$_{24}$ triethoxysilane, or C$_6$ to C$_{24}$ silane-triol. In an aspect, the adhesive for joining metal oxides to a conductive organic material is dodecyl trimethoxysilane, dodecyl triethoxysilane, or dodecyl silane-triol. Not to be limited by theory, these adhesive are thought to work by van der Waals interactions with the organic conductor material, or through polymerization with the conductor material to provide a terminal group consisting of either trimethoxysilane, triethoxysilane, or silane-triol, which will bind the electrocatalyst material strongly.

In aspects of the present disclosure, the adhesive layer is applied through a dip-coating process onto those substrates where the substrate is an inorganic conductive layer. The substrate material is simply dipped into a solution containing 1×10$^{-3}$ M to 0.5 M concentration of the SCA in question. After dipping, the substrate is then heated to a temperature between 80° C. and 120° C. to ensure appropriate bonding of the SCA to the metal itself. In those aspects where the conductive material is organic in nature, dip-coating the organic conductive material into a solution containing 1×10$^{-3}$ M to 0.5 M concentration of the SCA may be used with mild heating in an inert atmosphere (N$_2$ or Ar) at 50° C. to 80° C. In those aspects where polymerization of the conductive substrate occurs (such as with polyphenylene vinylene), 0.01-0.5 wt % of the SCA (compared to the monomer material used) may be incorporated (specifically the vinyl triethoxysilane, vinyl trimethoxysilane or vinyl trisilan-triol) into the polymerization matrix to incorporate it indirectly within the conductor material.

The devices of the present disclosure provide for, and include, a catalyst on the surface of said electrically conductive networks. In certain aspects, a catalyst may be a catalyst mixture comprising one or more catalysts. In other aspects, a catalyst mixture may comprise one or more catalysts and one or more co-catalysts. In another aspect, a catalyst mixture may comprise one or more catalysts and one or more additives. In a further aspect, a catalyst mixture may comprise one or more catalysts, one or more co-catalysts, and one or more additives. Catalyst mixtures may further comprise solubilizer, binders, viscosity modifiers, isotonizing agents, pH regulators, solvents, dyes, gelling agents, thickeners, buffers, and combinations thereof.

One of ordinary skill in the art would understand that the selection of the catalyst determines the type of electrocatalysis that occurs upon application of an electrical potential. As discussed above, hydroxyl radicals produced by electrocatalysis must be removed from the catalytic surface before they undergo reduction by free electrons on the catalyst or by other reactive species produced by catalysis. This forces them to combine to form hydrogen peroxide just beyond the catalyst. One of ordinary skill in the art would understand that the residence time of dry hydrogen peroxide gas on the electrically conductive network is determined by the thickness of the substrate, the angle of incidence of the airflow, and the airflow velocity.

In aspects according to the present disclosure, the catalyst on the surface of an electrically conductive network is a metal, a metal oxide, or mixtures thereof. Also provided for and included in the present disclosure are ceramic catalysts. Catalysts of the present disclosure include, but are not limited to, titanium dioxide, copper, copper oxide, zinc, zinc oxide, iron, iron oxide, or mixtures thereof. Suitable catalysts are provided, for example at Table 1. In some aspects, the catalyst is titanium dioxide in the form of anatase or rutile. In certain aspects, the titanium dioxide is the anatase form. In some aspects, the catalyst is titanium dioxide in the form of rutile. In other aspects, the titanium dioxide catalyst is a mixture of anatase and rutile. Also provided for, are catalysts on the surface that comprise tungsten trioxide (WO$_3$). Not to be limited by theory, the use an electric potential allows for the oxidation of water to hydroxyl radicals using a wider variety of materials that is available using a photocatalytic approach.

TABLE 1

| Catalysts having suitable Band-gap Energies | |
| --- | --- |
| Photo-catalyst | Band-gap energy (electron volts (eV)) |
| Si | 1.1 |
| WSe$_2$ | 1.2 |
| CuO | 1.21-1.51 |
| CdS | 2.4 |
| WO$_3$ | 2.4-2.8 |
| V$_2$O$_5$ | 2.7 |
| SiC | 3.0 |
| TiO$_2$ (rutile) | 3.02 |
| Fe2O$_3$ | 3.1 |
| TiO$_2$ anatase | 3.2 |
| ZnO | 3.2 |
| SRTiO$_3$ | 3.2 |
| SnO$_2$ | 3.5 |
| ZnS | 3.6 |
| BaTiO$_3$ | 3.2 |
| CaTiO$_3$ | 2.32 |
| SrTiO$_3$ | 3.75 |

In certain aspects, the catalyst may be tungsten oxide or a mixture of tungsten oxide with another metal or metal oxide catalyst. In some aspects, the catalyst is selected from the group consisting of tungsten(III) oxide, tungsten(IV) oxide ($WO_2$), tungsten(VI) oxide ($WO_3$), and tungsten pentoxide. In an aspect, the tungsten oxide is tungsten dioxide ($WO_2$). In another aspect, the catalyst may be a tungsten trioxide ($WO_3$) catalyst combined with a cesium co-catalyst. (See "Development of a High-performance Photocatalyst that is Surface-treated with Cesium," available on the internet at www(dot)aist(dot)go(dot)jp/aist_e/latest_research/2010/20100517/20100517.html).

Other catalysts suitable for use in the present devices include, but are not limited to metal oxides of the type $M^1M^2O_3$ where $M^1$ is typically a divalent cation and $M^2$ is a tetravalent cation (also known as perovskites). Examples of suitable metal oxides are titanates of alkaline earth metals such as calcium (Ca), strontium (Sr), and barium (Ba) 1. In an aspect, the catalyst comprises barium titanate ($BaTiO_3$) $E_g$=3.14 eV (direct). In an aspect, the catalyst comprises strontium titanate ($SrTiO_3$) $E_g$=3.75 eV (direct), 3.25 eV (indirect). In an aspect, the catalyst comprises calcium titanate ($CaTiO_3$) $E_g$=3.3-4.8 eV (direct).

The present disclosure provides for, and includes, catalysts that are polyoxometallates. Polyoxometallates are polyatomic ions that consist of three or more transition metal oxyanions that are linked together to form 3-D frameworks. These are considered nanoparticles in which a large degree of functionality can be incorporated due to the fact that multiple transition metals are utilized. By changing the type and quantity of metals involved, the bandgap can be engineered as noted in: S. Roy, S. Sarkar, J. Pan, U. Waghmare, R. Dhanya, C. Narayana, S. C. Peter in *Inorg. Chem.*, 2016, 55(7), 3364-3377.

The catalysts of the present disclosure may further include one or more co-catalysts. In certain aspects, the present disclosure provides for and includes using catalysts that are photocatalysts. Accordingly, suitable catalysts and methods to prepare catalysts to provide for catalysts suitable for devices having a light source that emits in the visible spectrum are known in the art and may be applied to the present electrically conductive network. See, Tukenmez, "Tungsten Oxide Nanopowders and Its Catalytic Activity under Visible Light Irradiation," Thesis, Department of Molecular Biology, Umea University, Sweden, (2013) available on the internet at www(dot)diva-portal(dot)org/smash/get/diva2:643926/FULLTEXT01.pdf; Kim et al., "Photocatalytic Activity of $TiO_2$ Films Preserved under Different Conditions: The Gas-Phase Photocatalytic Degradation Reaction of Trichloroethylene," Journal of Catalysis 194(2): 484-486 (2000); Blake et al., "Application of the Photocatalytic Chemistry of Titanium Dioxide to Disinfection and the Killing of Cancer Cells," Separation and Purification Methods 28(1):1-50 (1999); Sugihara et al., "Development of a Visible Light Responsive Photocatalyst using Tungsten Oxide under Indoor Lighting," National Institute of Advanced Industrial Science and Technology (AIST) (2008). Co-catalysts of the present disclosure include, but are not limited to, platinum, gold, silver, copper, nickel, cesium, or palladium. In some aspects, the co-catalyst is a noble metal selected from the group consisting of gold, platinum, silver, rhodium, ruthenium, palladium, osmium, and iridium. In an aspect, the co-catalyst is gold. In another aspect, the co-catalyst is silver. In yet another aspect, the co-catalyst is platinum. In another aspect, the co-catalyst is an extruded ceramic. In certain aspects, the co-catalyst is zirconium dioxide ($ZrO_2$). In some aspects, the co-catalyst is an extruded titanium dioxide ceramic (see Shon et al., "Visible Light Responsive Titanium Dioxide ($TiO_2$)—a review" available at epress.lib.uts.edu.au).

Co-catalysts of the present disclosure may be provided in various amounts relative to the catalyst. In general, co-catalysts can be provided at levels of up to about 5%. In certain aspects, the amount of co-catalyst is 5% or less, though mixtures of co-catalysts having a combined amount of up to 10% may be used in certain aspects. In certain aspects, up to 1.0% of the total mass of the catalyst may be a co-catalyst of the types described above. In some aspects, the total amount of co-catalyst is up to 0.05%. In yet other aspects, the co-catalyst is provided at between 0.005 and 0.05%. In some aspects, the co-catalyst is provided at between 0.01 and 0.05%. In another aspect, the co-catalyst is provided at between 0.01% to 0.02%. In certain aspects, the co-catalyst is provided a less than 0.05% of the total mass of the catalyst.

The catalysts of the present disclosure may further include one or more additives. In an aspect, an additive may be a hygroscopic additive. Not to be limited by theory, it is thought that the presence of a hydroscopic additive increases the local concentration of water on the catalytic surface and thereby provide for dry hydrogen peroxide gas production at lower humidity levels and improves the efficiency of DHP production at higher humidity levels. As provided herein, catalyst coatings having hygroscopic agents extend the efficiency of DHP generating devices and extends the range of relative humidities wherein the DHP generative device operates efficiently and can produce DHP at a rate sufficient to establish a steady state concentration of DHP of at least 0.005 ppm in a closed air volume of 10 cubic meters. In certain aspects, the relative humidity can be as low as 1%. In an aspect, the humidity of the ambient air is preferably above about 1% relative humidity (RH). In certain aspects the relative humidity can be from 1 to 99%. In other aspects, the humidity of the air flowing through the electrically conductive network is between 1% and 20% RH. In further aspects, the humidity of the air flowing through the electrically conductive network is at or above 5%. In other aspects, the humidity of the ambient air may be between about 10% and about 99% RH. In other aspects, the humidity of the ambient air may be between about 10% and about 99% RH. In certain aspects, the humidity of the air flow is less than 80%. In an aspect, the humidity is between 10% and 80%. In yet other aspects, the relative humidity is between 30% and 60%. In another aspect, the humidity is between 35% and 40%. In some aspects, the humidity of the air flowing through the electrically conductive network is between 56% and 59%.

In aspects according to the present disclosure, the hygroscopic additive may be selected from the group consisting of sodium bicarbonate, potassium bicarbonate, sodium carbonate, potassium carbonate, magnesium carbonate, magnesium bicarbonate, sodium hydroxide, potassium hydroxide, magnesium hydroxide, zinc chloride, calcium chloride, magnesium chloride, sodium phosphate, potassium phosphate, magnesium phosphate, carnallite ($KMgCl_3 \cdot 6(H_2O)$), ferric ammonium citrate, nylon, acrylonitrile butadiene styrene (ABS), polycarbonate, cellulose, poly(methyl methacrylate), and combinations thereof. In other aspects according to the present disclosure, the hygroscopic additive may be selected from the group consisting of sodium hydroxide, potassium hydroxide, magnesium hydroxide, zinc chloride, calcium chloride, magnesium chloride, sodium phosphate, potassium phosphate, magnesium phosphate, carnallite ($KMgCl_3 \cdot 6(H_2O)$), and combinations thereof.

In aspects according to the present disclosure, the hygroscopic additive may be a salt. In some aspects, the hygroscopic additive may be a hydroxide. In certain aspects, the hygroscopic additive may be sodium hydroxide, potassium hydroxide, or magnesium hydroxide. In some aspects, the hygroscopic additive may be a chloride. In certain aspects the hygroscopic additive may be zinc chloride, calcium chloride, or magnesium chloride. In yet other aspects, the hygroscopic additive may be a phosphate. In certain aspects, the hygroscopic phosphate may be sodium phosphate, potassium phosphate, or magnesium phosphate. It is understood that one or more hygroscopic compounds may be combined.

In general, additives can be provided at levels of up to about 5%. In certain aspects, the amount of additive is 5% or less, though mixtures of additives having a combined amount of up to 10% may be used in certain aspects. In certain aspects, up to 1.0% of the total mass of the catalyst may be an additives of the types described above. In some aspects, the total amount of additive is up to 0.05%. In yet other aspects, the additive is provided at between 0.005 and 0.05%. In some aspects, the additive is provided at between 0.01 and 0.05%. In another aspect, the additive is provided at between 0.01% to 0.02%. In certain aspects, the additive is provided at less than 0.05% of the total mass of the catalyst.

The present disclosure further provides for and includes a catalyst surface having a pH of 6.0 or greater. Not to be limited by theory, it is thought that the higher pH provides an improved source for oxidizable hydroxide ions during electrocatalysis thereby increasing the production of dry hydrogen peroxide gas. In an aspect, the pH of the catalyst surface is greater than pH 7.0. In another aspect, the pH of the surface is between 7.0 and 9.0. In an aspect, the pH of the catalyst surface is between 7.0 and 8.5. In an aspect, the pH of the catalyst surface is between 7.0 and 8.0. In an aspect, the pH of the catalyst surface is between 7.0 and 7.5. In another aspect, the pH of the surface is between 7.5 and 9.0. In an aspect, the pH of the catalyst surface is between 7.5 and 8.5. In an aspect, the pH of the catalyst surface is between 7.5 and 8.0. In another aspect, the pH of the surface is between 8.0 and 9.0. In an aspect, the pH of the catalyst surface is between 8.0 and 8.5. In certain aspects, the pH of the surface is at least 7.5. In certain aspects, the pH of the surface is at least 8.0.

Catalysts of the present disclosure, optionally including co-catalysts and additives may be prepared according to methods known in the art. Suitable co-catalysis and additives include silver nitrate, cerium oxide and zinc oxide. Additives are included to reduce, for example, bacterial growth and to prevent UV induced degradation of the catalyst and electrically conductive network. The catalysts, co-catalysts and additives of the present disclosure may be applied to a conductive network by a variety of methods including, but not limited to, gel sol methods, painting, dipping, and powder coating. In other aspects, the catalysts, co-catalysts and additives of the present disclosure may be applied to a conductive network by toll coating, tape casting, ultrasonic spray, and web-based coating. As provided herein, the method of applying the catalysts, co-catalysts and additives is suitable if it provides for, and includes, retaining the conductive network of the underlying electrically conductive network as recited above.

In an aspect, the catalyst mixture is applied to a conductive network using a sol-gel method comprising the use of an alcoholic metal salt as the catalytic material. In certain aspects, the metal salt is $Ti(OR)_4$. The sol-gel methods may further include co-catalysts such as $WO_3$, $SnO_2$, $Fe_2O_3$, or ZnO. The gel solution may be applied by dipping the conductive network into the gel solution or painting the solution onto the electrically conductive network. The thickness of the catalyst mixture applied to the substrate may be controlled by controlling the dipping speed or by providing one or more coats. After drying, the coated substrate may be baked and then sintered at high temperatures. In certain aspects, the catalytic mixture may further include noble metals or transition metals. In some aspects, the catalyst mixture may further include noble metals such as Au, Pd, Pt, or Ag, and some transition metals such as $MoO_3$, $Nb_2O_5$, $V_2O_5$, $CeO_2$, or $Cr_2O_3$.

The electrocatalytic devices of the present disclosure provide for, and include, an electrical power source. As provided herein, a power source may be a direct current (DC) power source. In an aspect, the DC power may be provided from a battery. In an aspect, the DC power source is a DC power supply, an AC-to-DC power supply, or a switched-mode power supply. Suitable batteries and power supplies are known in the art.

The present disclosure provides for, and includes, electrolytic systems having a power source that provides a wide range of voltages. Not to be limited by theory, as the potential required to produce DHP is on the order of a few electron volts (eV), the voltage necessary to drive the electrocatalytic reaction is expected to be extremely low. Electrocatalytic devices having a potential of about 0.01 V and a current of about 0.01 Amp are capable of producing DHP on a titanium dioxide coated copper mesh sail. While a low voltage compared to familiar electronic devices, it is anticipated that electrocatalytic devices can be powered by voltages orders of magnitude below 0.01 V and a current of 0.1 ampere. As provided herein, an electrical power source provides a voltage between $1 \times 10^{-6}$ volts (V) and 50,000 V. Practically, an upper limit of usable voltage for an electrolytic device using ambient air is determined by the power necessary to generate ozone electrolytically. As ozone is an undesirable toxic gas, with no known useful medical application in specific, adjunctive, or preventive therapy, it is to be avoided when producing DHP. The power of the devices of the present disclosure are limited only by considerations of safety to minimize and avoid electric shock. The power of the present devices is further limited by the necessity to avoid the production of ozone. Ozone can be produced, for example, using dielectric barrier discharge methods from air for example as described in U.S. Pat. No. 4,970,056, issued Nov. 13, 1990, to Wooten et al., U.S. Pat. No. 5,766,560, issued Jun. 16, 1998, to Cole. Ozone is also produced by arcing between electrodes. Accordingly the devices of the present disclosure are designed to operate at lower voltages that avoids arcing.

In aspects according to the present disclosure, the electrical power source is a power source providing between $1 \times 10^{-6}$ volts (V) and 50,000 V. In an aspect, the electrical power source provides at least $1 \times 10^{-6}$ volts (microV or $\mu$V). In another aspect, the electrical power source provides at least $1 \times 10^{-5}$ volts (V). In an aspect, the electrical power source provides at least $1 \times 10^4$ volts (V). In other aspects, the electrical power source provides at least $1 \times 10^{-3}$ volts (millivolt or mV). In yet other aspects, the electrically conductive network is supplied by an electrical power source providing a voltage of at least 0.01 V. In other aspects, the electrocatalytic devices are provide a voltage of at least 0.1 V. In an aspect, electrical power sources provide a voltage of at least 1 V. According to the present disclosure, the voltage of an electrical power source may be between 1 $\mu$V to 100 V. In other aspects, the voltage of an electrical power source may be between 1 µV to 110 V. In other aspects, the voltage of an electrical power source may be between 1 µV to 220 V. The present specification provides for, and includes, devices for the production of DHP wherein the voltage of the electrical power source may be between 1 mV to 110 V. According to the present disclosure, the voltage of an electrical power source may be between 1 mV to 100 V. In other aspects, the voltage of an electrical power source may be between 1 mV to 220 V. According to the present disclosure, the voltage of an electrical power source may be between 1 V to 110 V. In other aspects, the voltage of an electrical power source may be between 1 V to 220 V.

Given the low power requirements, the electrolytic devices of the present disclosure can be powered by standard alkaline batteries (e.g., 1.5V). Similarly, Nickel-Cadmium (Ni—Cd) and nickel-metal hydroxide batteries (1.2V) provide sufficient power for use as an electrical power source. In an aspect, the electrical power source is a lithium ion battery (3 V). Also provided for and included, are batteries providing higher voltages including 6 V, 9V, 12V, or higher. The electrical power sources of the present disclosure can be batteries placed in parallel or serially. Accordingly, given the low power requirements, the type, power and configuration of a battery to provide a suitable electrical power source is well known in the art.

In aspects of the present disclosure, a device for the production of dry hydrogen peroxide (DHP) comprises an electrically conductive network coated with a catalyst, an electrical power source, and a voltage regulator. In aspects of the present disclosure, a device for the production of dry hydrogen peroxide (DHP) comprises an electrically conductive network coated with a catalyst, an electrical power source, and a current regulator.

The present disclosure is not limited to battery powered devices but includes and provides for a DC power supply provided by an AC to DC power supply, a photovoltaic power supply or other direct current power source known in the art. In an aspect, the power supply is a variable voltage power supply. For example, a power supply that provides up to 30 V and 10 amps is suitable for devices of the present disclosure. In other aspects, high voltage power supplies may be used to generate DHP using the devices according to the present disclosure. As used herein the term "about" refers to ±10%.

The terms "comprises," "comprising," "includes," "including," "having," and their conjugates mean "including but not limited to."

The term "consisting of" means "including and limited to."

The term "consisting essentially of" means that the composition, method, or structure may include additional ingredients, steps, and/or parts, but only if the additional ingredients, steps, and/or parts do not materially alter the basic and novel characteristics of the claimed composition, method, or structure.

As used herein, the singular form "a," "an," and "the" include plural references unless the context clearly dictates otherwise. For example, the term "a compound" or "at least one compound" may include a plurality of compounds, including mixtures thereof.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques, and procedures for accomplishing a given task including, but not limited to, those manners, means, techniques, and procedures either known to or readily developed from known manners, means, techniques, and procedures by practitioners of the agronomic, chemical, pharmacological, biological, biochemical, and medical arts. Methods may include single or multiple steps.

In aspects according to the present disclosure, an enclosure comprises a volume having at least one opening for the entry of air and at least one opening for the discharge of air having dry hydrogen peroxide gas. In some aspects, the enclosure may be prepared from polyethylene, polypropylene, polystyrene, nylon, or polyvinyl chloride.

As used herein, in other aspects, an enclosure can comprise a heating, ventilating, and air conditioning (HVAC) system. In other aspects, a device for producing DHP is a device placed in an HVAC system during construction. Suitable HVAC systems and appropriate standards are known in the art, for example standards developed by the Sheet Metal & Air Conditioning Contractors' National Association (SMACNA). As provided herein, devices suitable for installation into an HVAC system include the elements recited for standalone devices but wherein the enclosure and air distribution system are provided by the HVAC system. Devices suitable for installation into an HVAC system may further comprise an additional air distribution system (e.g., separate from the air distribution system of the HVAC system as a whole). Devices suitable for installation into an HVAC system may further comprise one or more additional filters to prevent contamination with dust or chemicals.

In aspects according to the present disclosure, a device includes an air distribution mechanism to provide an airflow. In some aspects, the air flow is a continuous airflow. In other aspects, the air flow is discontinuous. In aspects according to the present disclosure, the airflow of the device may be a laminar flow of air though an electrically conductive network. In other aspects, the airflow may be turbulent flow through an electrically conductive network. In yet another aspect, the airflow may be transitional. In aspects according to the present disclosure, the airflow of the device may have a Reynolds number of less than 2300. In another aspect, the airflow of the device may have a Reynolds number of between 2300 and 4000. In yet another aspect, the airflow of the device may have a Reynolds number of greater than 4000.

In some aspects, an air distribution mechanism is placed upstream of an electrically conductive network and provides an airflow through the network. In other aspects, an air distribution mechanism is placed after an electrically conductive network and pulls the air through the network. In certain aspects, the airflow is provided by one or more fans. In yet another aspect, the air flow is provided by a climate control system such as an air conditioner, a furnace, or a heating, ventilation, and air-conditioning (HVAC) system.

Not to be limited by theory, it is believed that the electrocatalytic devices of the present disclosure generate DHP through a similar reaction mechanism to the production of DHP through photocatalysis. See Table 2. At the same time, electrocatalytic devices are not susceptible to photolysis reactions as shown in Table 3.

TABLE 2

| Half Reactions for the Catalytic Production of DHP | |
| --- | --- |
| Half Reaction | Std. Reduction Potential (eV) |
| Oxidative Pathway | |
| $h\nu \rightarrow h^+ + e^-$ (on $TiO_2$ catalyst) | $\leq -3.2$ |
| $h\nu \rightarrow h^+ + e^-$ (on $TiO_2$ catalyst with co-catalyst) | $\leq -2.85$ |
| $h^+ + H_2O \rightarrow OH^* + H^+$ | 2.85 |
| $2OH^* \rightarrow H_2O_2$ | 1.77 |
| Reductive Pathway | |
| $e^- + O_2 \rightarrow O_2^-$ (First Step is non-Spontaneous) | $-0.13$ |
| $2H^+ + 2e^- + O_2 \rightarrow H_2O_2$ (Overall Reaction) | 0.70 |
| Side reactions that consume DHP | |
| $h^+ + e^-$ (on $TiO_2$ catalyst) $\square$ Heat | $\leq 3.2$ |
| $OH^* + e^- + H^+ \rightarrow H_2O$ | 2.02 |
| $2OH^* + H_2O_2 \rightarrow 2H_2O + O_2$ | 2.805 |
| $H_2O_2 + 2H^+ + 2e^- \rightarrow 2H_2O$ | 1.78 |
| $e^- + H_2O_2 \rightarrow OH^* + OH^-$ | 0.71 |

TABLE 3

| Reactions in Photocatalytic Plasmas avoided in the Electrocatalytic Process | |
| --- | --- |
| $O_2 + h\nu \rightarrow 2O^*$ (by Photolysis) | $-5.13$ |
| $2O^* + 2O_2 \rightarrow 2O_3$ | 2.99 |
| $O_3 + 2H^+ + 2e^- \rightarrow O_{2(g)} + H_2O$ | 2.075 |
| $O_3 + H_2O + 2e^- \rightarrow O_{2(g)} + 2OH^-$ | 1.24 |
| $H_2O_2 + h\nu \rightarrow 2OH^*$ (by Photolysis) | 1.77 |
| Ozone Destruction of Hydrogen Peroxide | |
| $O_3 + H_2O_2 \rightarrow H_2O + 2O_2$ | 1.381 |

Devices of the present disclosure are provided with an airflow sufficient to minimize the time of contact with the catalytic surface present on a conductive network.

The devices of the present disclosure include and provide for air distribution mechanisms capable of providing an airflow having a velocity from about 5 nanometers/second (nm/s) to 10,000 nm/s as measured at the surface of the electrically conductive network. In certain aspects, the flow rate is between 5 nm/s to 7,500 nm/s. In certain aspects, the flow rate is between 5 nm/s to 5,000 nm/s. In certain aspects, the flow rate is between 5 nm/s to 2,500 nm/s. In certain aspects, the flow rate is between 5 nm/s to 5,000 nm/s. In certain aspects, the flow rate is between 5 nm/s to 1,000 nm/s. In other aspects, the flow rate of the air at the electrically conductive network is between 5 and 15 nm/s. In another aspect, the air flow velocity is between 15 nm/s to 30 nm/s. In an aspect, the air flow velocity is between 30 nm/s to 50 nm/s. In an aspect, the air flow velocity is between 50 nm/s to 75 nm/s. In an aspect, the air flow velocity is between 75 nm/s to 100 nm/s. In an aspect, the air flow velocity is between 100 nm/s to 250 nm/s. In an aspect, the air flow velocity is between 250 nm/s to 500 nm/s. In an aspect, the air flow velocity is between 500 nm/s to 750 nm/s. In an aspect, the air flow velocity is between 750 nm/s to 1000 nm/s. In an aspect, the air flow velocity is between 1000 nm/s to 2,500 nm/s. In an aspect, the air flow velocity is between 2,500 nm/s to 5,000 nm/s. In an aspect, the air flow velocity is between 5,000 nm/s to 7,500 nm/s. In an aspect, the air flow velocity is between 7,500 nm/s to 10,000 nm/s. In certain aspects, suitable devices for HVAC systems are designed to handle air flows up to 40,000 cubic feet per minute (CFM).

As provided herein, the maximal airflow through the electrically conductive network for the production of DHP is limited by the reaction of hydroxyl radicals into hydrogen peroxide and the production rate of DHP drops. Not to be limited by theory, it is thought that the hydroxyl radicals are maintained in a sufficiently dilute balance which favors their combination to form hydrogen peroxide yet minimizes decomposition into water and oxygen. The maximal flow limitation depends on the structure of the electrically conductive network, applied voltage, resistance, current type (DC or AC), the catalyst, the relative humidity and other variables that are currently being further explored. Currently, the air flow for DHP production can be optimized by holding the current and voltage of the electrically conductive network constant and varying the air-flow. The production of DHP is then measured at a distance of at least five feet and the airflow adjusted to maximize production.

The present disclosure provides for, and includes, airflow rates through the electrically conductive network of greater than 100 CFM. In an aspect, DHP generating devices for an HVAC system are provided an airflow on average of 145 CFM. For a standalone DHP generating device, the air distribution mechanism provides for an average of 115 CFM through the electrically conductive network.

In aspects, the direction of the airflow at the air permeable structure may be provided at an angle relative to the air permeable structure (the angle of incidence).

In aspects according to the present disclosure, the airflow through the electrically conductive network is humid air. In certain aspects, the humid air is ambient humid air. In other aspects, the humidity of the air flowing through the electrically conductive network is at or above 20% RH. In further aspects, the humidity of the air flowing through the electrically conductive network is at or above 30%. In some aspects, the relative humidity is between 35% and 40%. In other aspects, the humidity of the ambient air may be between about 20% and about 99% RH. In other aspects, the humidity of the ambient air may be between about 20% and about 99% RH. In certain aspects, the humidity of the air flow is less than 80%. In an aspect, the humidity is between 20% and 80%. In yet other aspects, the relative humidity is between 30% and 60%. In another aspect, the humidity is between 35% and 40%. In some aspects, the humidity of the air flowing through the electrically conductive network is between 56% and 59%. In aspects according to the present disclosure the relative humidity is between 20% and 80%.

The electrocatalytic devices of the present disclosure provide for, and include devices that operate under low humidity conditions. As used herein, a "low humidity condition" is a humidity of less than 20% RH. In other aspects, the humidity of the air flowing through the electrically conductive network is between 1% and 20% RH. In further aspects, the humidity of the air flowing through the electrically conductive network is at or above 10%. In some aspects, the relative humidity is between 5% and 20%. In other aspects, the humidity of the ambient air may be between about 5% and about 15% RH. In other aspects, the humidity of the ambient air may be between about 10% and about 20% RH.

In aspects according to the present disclosure, the airflow through the electrically conductive network may be supplemented by humidification. In certain aspects, ambient air is supplemented by a humidifier to provide an airflow having at least 20% humidity. In certain aspects, the relative humidity of the air flowing through permeable substrate structure is maintained at between 20% and 80%. In another aspect, the air may be humidified to 30% or higher relative humidity. In some aspects, the relative humidity of the humidified airflow is between 35% and 40%. In other aspects, the humidity of the humidified air may be between about 20% and about 99% or between about 30% to 99% RH. In an aspect, the relative humidity after humidification is less than 80%. In an aspect, the relative humidity after humidification is between 20% and 80%. In yet other aspects, the relative humidity after humidification is between 30% and 60%. In another aspect, the relative humidity after humidification is between 35% and 40%. In some aspects, the relative humidity after humidification of the air flowing through the electrically conductive network is between 56% and 59%.

In aspects according to the present disclosure, a device may provide an airflow that recirculates air within a space. In this mode, the device will self-regulate DHP levels by reducing excess DHP to humidity and oxygen as it recirculates through the device, instead of reducing oxygen to DHP. In other aspects, a device may provide, in whole or in part, an airflow comprising fresh air. In certain aspects, the device includes and provides for a source of fresh air either from the outside or from a separate filtered flow of air. In aspects according to the present disclosure, the device may be included in an air conditioning and ventilation system that recirculates air within a room or building. In some aspects, the recirculating room or building air may be supplemented with fresh outside air.

In aspects according to the present disclosure, the electrically conductive network having a catalyst on its surface is between about 1 μm and about 10 mm in total thickness (e.g., the combined thickness of non-conductive layer 140 (if present), conductive layer 125, and catalytic layer 135). Adhesive layers 130 or 126 do not contribute appreciably to the total thickness. In certain aspects, the maximum thickness of an electrically conductive network is 5 mm. In an aspect, the thickness of the electrically conductive network is between 100 and 200 μm. In an aspect, the thickness of the electrically conductive network is between 145 and 150 μm. In an aspect, the thickness of the electrically conductive network is between 5 μm and 15 μm. In another aspect, the thickness of the electrically conductive network is between 15 μm and 30 μm. In an aspect, the thickness of the electrically conductive network is between 20 μm and 40 μm. In an aspect, the thickness of the electrically conductive network is about 30 μm. In a further aspect, the thickness of the electrically conductive network is between 30 μm and 50 μm. In yet another aspect, the thickness of the electrically conductive network is between 50 μm and 75 μm. In an aspect, the thickness of the electrically conductive network is between 75 μm and 100 μm. In yet another aspect, the thickness of the electrically conductive network is between 100 μm and 250 μm. In a further aspect, the thickness of the electrically conductive network is between 250 μm and 500 μm. In certain aspects, the thickness of the electrically conductive network is between 500 μm and 750 μm. In aspects according to the present disclosure, the thickness of the electrically conductive network having a catalyst on its surface is between about 5 μm and 100 μm. In an aspect, the thickness of the electrically conductive network having a catalyst on its surface is between about 15 μm and 100 μm. In an aspect, the thickness of the electrically conductive network having a catalyst on its surface is between about 20 μm and 100 μm. In an aspect, the thickness of the electrically conductive network having a catalyst on its surface is between about 20 μm and 75 μm. In an aspect, the thickness of the electrically conductive network having a catalyst on its surface is between about 20 nm and 50 nm.

The present disclosure provides for electrically conductive networks having a catalyst on its surface that comprises a conductive layer 125 and a catalytic layer 135. In aspects, the conductive layer 125 is between $50 \times 10^{-9}$ meters (nm) and $2 \times 10^{-6}$ meters (μm). In aspects, the conductive layer 125 is between 100 nm and 2 μm. In aspects, the catalytic layer is between 2.0 and 750 nm thick.

In certain aspects according to the present disclosure, the electrically conductive network having a catalyst on its surface is between about 750 micrometers (μm) and about 1000 μm in total thickness. In an aspect, the thickness of the electrically conductive network is between 1000 and 2500 μm. In another aspect, the thickness of the electrically conductive network is between 2500 μm and 5000 μm. In an aspect, the thickness of the electrically conductive network is between 5000 μm and 7500 μm. In a further aspect, the thickness of the electrically conductive network is between 7500 μm and 10000 μm.

Also provided for and included in the present disclosure are devices having an electrically conductive network configured as a mesh. As used herein, a "mesh" refers to a network of spaces in a net or network comprising a network of cords, threads, or wires. The cords and threads can comprise a variety of known polymers (e.g., polypropylene (PP), polyethylene (PE), high density polyethylene (HDPE), medium-density polyethylene (MDPE), low-density polyethylene (LDPE), polypropylene/polyethylene (PP/PE) blends, cross-linked polyethylene (PEX), ultra-high molecular weight polyethylene (UHMWPE) etc.) that have a conductive material impregnated within the fiber or are coated with a conductive material after formation of the strand. In certain aspects, the conductive material can be applied to the fabric after weaving or non-oriented cloth production. In some aspects, a mesh may be a woven cloth or fabric. Various weaves and meshes are known in the art to produce a mesh having round, triangular, square, polygonal, polyhedron, ellipsoid, or spherical openings suitable for providing for a flow of air. In some aspects, a mesh may be a woven wire. In certain aspects, a mesh may be a woven honeycomb shape. In other aspects, a mesh may be a nonwoven wire, metal impregnated polymer strand, metal coated strand, or metal coated fabric.

The present disclosure provides for and includes, electrically conductive networks having a mesh with an open area of between 20% and 60% and a maximal thickness of catalyst up to 750 nm. Also included are electrically conductive networks having a mesh with an open area of about 40%. In an aspect the mesh opening is about 200 microns and the thread thickness is about 152 microns.

In aspects according to the present disclosure, a mesh is greater than 20 strands per centimeter. In certain aspects, the open area of the mesh is less than about 120 strands per centimeter. In an aspect, the mesh opening is about 200 microns (μm) corresponding to about 41% open area for a thread thickness of about 150 microns. In certain aspects, the mesh includes an open area of at least about 20% and a thread thickness of about 48 microns. In certain aspects, the mesh has a hole size of between 25 μm and 220 μm and having an open area of between 20% and 40%. In other aspects, the mesh has a hole size of between 25 μm and 220 μm and a thread thickness of between 48 μm and 175 μm.

In aspects according to the present disclosure, an air permeable conductive network comprises a meshwork or a conductive fabric having a mesh of at least 100 cells (spaces) per square inch (cpsi). In aspect, the mesh or network has between 100 and 1000 cpsi. In an aspect, the has at least 200 cpsi. In another aspect, the mesh has at least 300 cpsi. In other aspects, the mesh has at least 400 cpsi. Other aspects provide for air permeable conductive networks having 500 cpsi. In yet another aspect, the air permeable conductive network has a mesh of at least 600 cpsi. Also provided in an aspect, are air permeable conductive networks having at least 700 cpsi. In an aspect, the mesh has at least 800 cpsi. In a further aspect, the mesh is 900 cpsi. The air permeable conductive networks of the present disclosure can have a range of meshes, from 100 to 500 cpsi, 200 to 500 cpsi, 300 to 600 cpsi, 300 to 700 cpsi and 200 to 500 cpsi.

In aspects according to the present disclosure, a mesh may be prepared having a regular, repeating pattern of spaces in the net or network. In other aspects, a mesh of the present disclosure may have an irregular or non-repeating pattern of spaces. In yet another aspect, the mesh may be a random array of open spaces. In another aspect, the mesh may have a honeycomb appearance. In aspects according to the present disclosure, the open spaces within the mesh are round, triangular, square, polygonal, polyhedron, ellipsoid, or spherical.

According to the present disclosure, an electrically conductive network comprises a mesh having a percentage of open area of between 20% and 60% after coating. In another aspect, the conductive network may have an open area of between 20% and 30%. In an aspect, the conductive network may have an open area of between 30% and 40%. In a further aspect, the conductive network may have an open area of between 40% and 50%. In yet another aspect, the conductive network may have an open area of between 50% and 60%. In certain aspects, the percentage of open area of the conductive network may be between 36% and 38%. In an aspect, the percentage of open area is about 37%.

The present disclosure provides for and includes for electrically conductive networks having a combined thickness of between 1 μm and 7 mm and having an open area of a mesh between 10% and 60%. In an aspect, the substrate structure may have a thickness selected from the group consisting of 5 μm to 15 μm, 15 μm to 30 μm, 20 μm to 40 μm, 30 μm to 50 μm, 50 μm to 75 μm, 75 μm to 100 μm, 100 μm to 250 μm, 250 μm to 500 μm, and 500 μm to 750 μm and having an open area of mesh between 10% and 20%. In an aspect, the substrate structure may have a thickness selected from the group consisting of 5 μm to 15 μm, 15 μm to 30 μm, 20 μm to 40 μm, 30 μm to 50 μm, 50 μm to 75 μm, 75 μm to 100 μm, 100 μm to 250 μm, 250 μm to 500 μm, and 500 μm to 750 μm thick and has an open area of mesh between 20% and 30%. In an aspect, the substrate structure may have a thickness selected from the group consisting of 5 μm to 15 μm, 15 μm to 30 μm, 20 μm to 40 μm, 30 μm to 50 μm, 50 μm to 75 μm, 75 μm to 100 μm, 100 μm to 250 μm, 250 μm to 500 μm, and 500 μm to 750 μm thick and has an open area of mesh between 30% and 40%. In an aspect, the substrate structure may have a thickness selected from the group consisting of 5 μm to 15 μm, 15 μm to 30 μm, 20 to 40 μm, 30 μm to 50 μm, 50 μm to 75 μm, 75 μm to 100 μm, 100 μm to 250 μm, 250 μm to 500 μm, and 500 μm to 750 μm thick and has an open area of mesh between 40% and 50%. In an aspect, the substrate structure may have a thickness selected from the group consisting of 5 μm to 15 μm, 15 μm to 30 μm, 20 to 40 μm, 30 μm to 50 μm, 50 μm to 75 μm, 75 μm to 100 μm, 100 μm to 250 μm, 250 μm to 500 μm, and 500 μm to 750 μm thick and has an open area of mesh between 50% and 60%. In an aspect, the substrate structure may have a thickness selected from the group consisting of 5 μm to 15 μm, 15 μm to 30 μm, 20 μm to 40 μm, 30 μm to 50 μm, 50 μm to 75 μm, 75 μm to 100 μm, 100

μm to 250 μm, 250 μm to 500 μm, and 500 μm to 750 μm thick and has an open area of mesh between 36% and 38%.

Suitable electrically conductive networks for coating with a catalyst mixture according to the present disclosure include meshes, such as woven cloth or fabric or unwoven cloth or fabric. As provided herein, coating of a suitable mesh with a catalyst mixture requires that the mesh not be occluded and that the mesh retain an open area of between 20% and 60% as provided above.

Electrically conductive networks of the present disclosure may be prepared from polymers, carbon fibers, fiberglass, natural fibers, metal wires, and other materials that can be prepared as a mesh. For non-conductive materials (generally polymers, fiberglass, natural fibers) one or more metals can be incorporated into the fibers themselves prior to forming the mesh, or one or more metals can be applied to the surface of the finished network.

In aspects according to the present disclosure, a mesh may be an extruded mesh (also called "extruded netting"). In an aspect, an extruded mesh may be a bi-planar extruded mesh. In another aspect, the extruded mesh may be a mono-planar mesh. Extruded mesh may comprise a netting having a variety of apertures (hole sizes), weights, and thicknesses. Extruded meshes may be prepared from polypropylene (PP), polyethylene (PE), high density polyethylene (HDPE), medium-density polyethylene (MDPE), low-density polyethylene (LDPE), polypropylene/polyethylene (PP/PE) blends, cross-linked polyethylene (PEX), ultra-high molecular weight polyethylene (UHMWPE). The extruded nettings of the present disclosure may be prepared from a conductive material or coated after formation with a conductive material.

In an aspect, a mesh suitable for coating according to the present disclosure is a polymer. In an aspect the mesh may be nylon, polybutylene terephthalate (PBT), polyester, polyethylene, polypropylene, polytetrafluoroethylene (PTFE), polypropylene/polyethylene (PP/PE) blends or synthetic yarns or fibers.

Meshes according to the present disclosure may be a metal mesh or a ceramic mesh. Suitable metal meshes include electroformed screens. Electroformed screens suitable for the preparation of catalyst coated electrically conductive networks according to the present disclosure are available from, for example, Industrial Netting (Minneapolis, Minn.). Electroformed screens may have hole sizes ranging from 8 microns to 5000 microns or more. In certain aspects, the electroformed screen ranges from 36% to 98% open. In some aspects, the electroformed screen ranges from 36% to 98% open and has a thickness of between about 20 nm and 75 nm.

One of ordinary skill in the art would recognize that the production of ozone would result in the reduction of DHP gas to water and oxygen:

$$O_3 + H_2O_2 \rightarrow H_2O + 2O_2$$

In certain aspects, devices of the present disclosure may be degraded by the presence of contaminants such as dust, pollen, bacteria, spores, and particles that can occlude the open spaces of a mesh of the electrically conductive network. Similarly, volatile organic compounds (VOCs) which can react with reactive species, including hydrogen peroxide, decrease the production of DHP and the distribution of DHP to a space. Notably, while VOCs can be effectively reduced in a space by DHP produced devices of the present disclosure, VOCs introduced into the device itself are preferably minimized or eliminated altogether. Accordingly, to maintain the efficiency of the devices and to maximize DHP production, devices of the present disclosure may include one or more filters. As will be noted, the selection of the filters may be determined by the application and the type of space to be treated using DHP. For example, a clean room in which air is already treated to eliminate dust, VOCs, and other contaminates could employ a device having an enclosure, an air distribution mechanism, an electrical power source, and an electrically conductive network having a catalyst on its surface without requiring a prefilter. In contrast, a device for home use might require a dust filter and might further require a carbon filter to absorb VOCs. In certain aspects, the inclusion of an additional filter provides for the extended life of the air permeable catalyst coated substrates and provides for extended production of DHP.

Filters used to purify air unrelated to DHP generation are dependent on the air quality of the location in which the device is used. Inside an HVAC system with high quality air achieved by the filters of the HVAC system, no filters may be necessary before the air flow passes through the electrically conductive network of the DHP device itself. The same holds true for stand-alone devices operating in areas where there is high air quality. When necessary, filters are generally selected from those known in the art that can achieve the filtration required with as little impedance of air flow necessary. Filters are further selected from those known in the art so that the filter itself does not introduce particulates or gasses into the airstream. Suitable filters that combine the functions of removing particulates as well as gaseous contaminants are known in the art. Filters require replacement regularly, with a frequency determined by the load placed upon the filter due to higher air quality (less frequent replacement) or lower air quality (more frequent replacement).

In most applications three filtration concerns are applicable. In certain applications, particulates or dust can foul the substrate matrix and the catalyst itself, so a particulate filter sufficient to the needs of the location may be used. In certain common aspects, a high air flow, pleated MERV 18 filter is employed. In other applications, volatile organic hydrocarbons may require filtration and this may be accomplished using a number of different activated charcoal or carbon impregnated filters that are known in the art. In yet other applications, certain inorganic gasses such as nitrogen oxides need to be removed by filtration. To remove nitrogen oxides, a zeolite filter is usually employed. In some aspects, the DHP device includes impregnated zeolite filters that are capable of removing volatile organic hydrocarbons and nitrogen oxides in a single, combined material and stage. Suitable filters are known in the art that can remove particles of various sizes that would otherwise block the electrically conductive network or contaminate and inactivate the catalytic surface.

In aspects of the present disclosure, devices may further include one or more filters designed to remove contaminants selected from nitrogen oxides (NOx), sulfur oxides (SOx), volatile organic compounds, dust, bacteria, pollen, spores, and particles. In certain aspects, the device includes one or more filters selected from an organic vapor filter, a particulate filter, a high efficiency filter, a hydrophobic filter, an activated charcoal filter, or a combination thereof.

In certain aspects, pre-filters remove volatile organic compounds, NOx, and SOx. In some aspects, the filters remove aldehydes such as formaldehyde or acetaldehyde. In other aspects, the filters remove VOCs including toluene, propanol, and butene. In yet other aspects, pre-filters remove the mono-nitrogen oxides NO and $NO_2$ (e.g., NOx). In other aspects, pre-filters remove sulfur and oxygen containing compounds known as SOx. SOx compounds removed by filters of the present disclosure include SO, $SO_2$, $SO_3$, $S_7O_2$, $S_6O_2$, $S_2O_2$, or combinations thereof. Prefilters of the present disclosure may be employed to remove any combination of VOCs, NOx, and SOx.

In certain aspects, the devices include a filter comprising a microporous aluminosilicate mineral. In an aspect, a filter of the present device may be a zeolite filter. In an aspect, the zeolite may be analcime, chabazite, clinoptilolite, heulandite, natrolite, phillipsite, or stilbite. In certain aspects, the zeolite may be a synthetic zeolite. In an aspect, the device includes a zeolite filter for the removal of NOx, SOx, or both. Suitable filters are known in the art.

In other aspects, the devices include a filter comprising a particulate filter. In certain aspects, the particulate filter is a 3M ultra allergan filter. A suitable example of a particle filter can be obtained from Air Filters, Inc, which provides Astro-cell mini-pleat filters. One of ordinary skill in the art would be able to select filters that provide suitable air flow levels and resistance to air flow to provide for a sufficient air flow through the electrically conductive network as recited above.

In yet other aspects, suitable filters for devices of the present disclosure include carbon filters, charcoal filters, or activated carbon filters. In some aspects, the filter is a GAC (granular activated carbon) carbon filter. In certain aspects, an impregnated carbon filter is included in a device to remove hydrogen sulfides ($H_2S$) and thiols. Suitable impregnated carbon filters are known in the art.

Air filtration in devices according to the present disclosure provide for air flows across the electrically conductive network layer having low levels of contaminants and electrocatalysis inhibitors.

The present disclosure provides for, and includes, methods of using the electrolytic DHP producing devices for the reduction of microbes, volatile organic compounds, (VOCs), and insects as previously reported using photocatalytic devices. The present devices, given their low power requirements, further provide for methods that apply DHP technology to remote locations. In an aspect, electrolytic DHP producing devices can be made portable and wearable. In an aspect, the present disclosure provides for a method of providing a device comprising an electrically conductive network coated with a catalyst and an electrical power source that provides an electrical potential to said electrically conductive network, providing a flow of humid air through said electrically conductive network to prepare a DHP containing airflow, and directing said DHP containing airflow in to an enclosed environment. After a period of time, DHP accumulates in the environment and acts to reduce microbial levels. In an aspect, the DHP is provided to an environment to reduce the levels of insects and arthropods, either by killing or repelling them. The period of time before accumulation of DHP may vary with the environment, the number of devices, their size, air turnover and other factors. An important factor is the environment itself. Environments having high levels of VOCs require additional time to develop a steady level of DHP as the VOCs first need to be eliminated.

The devices of the present disclosure provide for, and include, a method for microbial control of an environment comprising: (a) generating a gas comprising DHP that is substantially free of hydration, ozone, plasma species, and/or organic species; (b) directing the DHP into the environment such that the hydrogen peroxide gas acts to provide microbial control. The devices of the present disclosure provide for, and include, a method for microbial disinfection of an environment comprising: (a) generating a gas comprising DHP that is substantially free of hydration, ozone, plasma species, and/or organic species; (b) directing the DHP into the environment such that the hydrogen peroxide gas acts to provide microbial disinfection. The devices of the present disclosure provide for, and include, a method for microbial remediation of an environment comprising: (a) generating a gas comprising DHP that is substantially free of hydration, ozone, plasma species, and/or organic species; (b) directing the DHP into the environment such that the hydrogen peroxide gas acts to provide microbial remediation.

The devices of the present disclosure provide for the preparation of environments having DHP levels of up to 200 ppb (0.2 ppm). In certain aspects, the amount of DHP may vary from about 0.001 ppm (e.g., 1 ppb) to about 1.0 ppm (1000 ppb), more particularly, from about 5 ppb to about 200 ppm, in the environment. In certain aspects, the amount of DHP may vary from about 1 ppb to about 100 ppb. DHP levels of 10 ppb using a feed of untreated air containing absolute humidity as low as 3.5 mg/L can consistently be achieved. More particularly, DHP levels from about 5 ppb to about 100 ppb using humid re-circulated air, can be produced in the environment to be treated.

EMBODIMENTS

Embodiment 1: A device for the production of dry hydrogen peroxide (DHP) comprising:
    a. an electrically conductive network coated with a catalyst;
    b. an electrical power source.

Embodiment 2: The device of Embodiment 1, further comprising an air distribution mechanism.

Embodiment 3: The device of Embodiments 1 or 2, wherein said electrically conductive network is an air permeable conductive network.

Embodiment 4: The device of any one of Embodiment 1 to 3, wherein said air permeable conductive network comprises a meshwork or a conductive fabric.

Embodiment 5: The device of any one of Embodiments 1 to 4, wherein said meshwork is a metal meshwork comprising a metal selected from the group consisting of copper, annealed copper, silver, gold, aluminum, tungsten, zinc, nickel, iron, platinum, tin, titanium, grain oriented electrical steel, stainless steel, and nichrome.

Embodiment 6: The device of Embodiment 4, wherein said meshwork is a meshwork comprising carbon graphite.

Embodiment 7: The device of any one of Embodiments 1 to 6, wherein said electrically conductive network has a resistivity ($\rho$) between $1.5 \times 10^{-8}$ ohm-meter ($\Omega \cdot$m) and $3 \times 10^{-3}$ ohm-meter ($\Omega \cdot$m) at 20° C.

Embodiment 8: The device of any one of Embodiments 1 to 7, wherein said electrically conductive network has a conductivity ($\sigma$) between $6.3 \times 10^{7}$ Siemens per meter (S/m) and $1 \times 10^{5}$ S/m at 20° C.

Embodiment 9: The device of Embodiment 3, wherein said conductive fabric is a woven or non-woven fabric.

Embodiment 10: The device of Embodiment 3 or 9, wherein said conductive fabric is a metal coated fabric comprising nylon, polyester coated with a metal selected from the group consisting of copper, annealed copper, silver, gold, aluminum, tungsten, zinc, nickel, iron, platinum, tin, titanium, grain oriented electrical steel, stainless steel, and nichrome.

Embodiment 11: The device of Embodiment 5, wherein said metal meshwork is a copper meshwork.

Embodiment 12: The device of any one of Embodiments 1 to 11, wherein said an electrical power source is a direct current (DC) power source, an alternating current (AC) power source or a Modulated Alternated Current (MAC) power source.

Embodiment 13: The device of Embodiment 12, wherein said direct current power source is a battery, a DC power supply, an AC-to-DC power supply, or a switched-mode power supply.

Embodiment 14: The device of Embodiment 12, wherein said AC power source is an AC power supply or an AC adapter.

Embodiment 15: The device of any one of Embodiments 1 to 14, wherein said power supply provides a voltage between 0.001 Volts (V) and 50,000 V.

Embodiment 16: The device of any one of Embodiments 1 to 15, wherein said power supply provides an amperage of between 0.01 Amp (A) and 100 A.

Embodiment 17: The device of any one of Embodiments 4 to 16, wherein said air permeable conductive network comprises a meshwork or a conductive fabric having a mesh of at least 100 cells (spaces) per square inch (cpsi).

Embodiment 18: The device of any one of Embodiments 4 to 17, wherein said air permeable conductive network comprises a meshwork or a conductive fabric having a nominal hole size ranging from 50 microns to 1200 microns.

Embodiment 19: The device of any one of Embodiments 4 to 18, wherein said air permeable conductive network comprises a meshwork or a conductive fabric comprises a mesh having a percentage of open area of between 10% and 60% after coating with said catalyst.

Embodiment 20: The device of any one of Embodiments 4 to 19, wherein said air permeable conductive network has a catalyst thickness of between 5 nm and 750 nm and having an open area of a mesh between 10% and 60%.

Embodiment 21: The device of any one of Embodiments 1 to 20, wherein said catalyst is a metal oxide.

Embodiment 22: The device of any one of Embodiments 1 to 21, wherein said catalyst is a metal oxide that is titanium dioxide, copper oxide, zinc oxide, iron oxide, tungsten oxide, or a mixture thereof.

Embodiment 23: The device of any one of Embodiments 1 to 22, wherein said catalyst is titanium dioxide that is in the form of anatase or rutile.

Embodiment 24: The device of any one of Embodiments 1 to 23, wherein said catalyst is tungsten oxide that is tungsten (III) oxide, tungsten (IV) oxide ($WO_2$), tungsten (VI) oxide ($WO_3$), or tungsten pentoxide.

Embodiment 25: The device of any one of Embodiments 1 to 24, wherein said catalyst further comprises a co-catalyst selected from platinum, gold, silver, copper, nickel, cesium, palladium, rhodium, ruthenium, osmium, or iridium.

Embodiment 26: The device of any one of Embodiments 1 to 25, wherein said catalyst further comprises a hygroscopic additive be selected from the group consisting of sodium hydroxide, potassium hydroxide, magnesium hydroxide, zinc chloride, calcium chloride, magnesium chloride, sodium phosphate, potassium phosphate, magnesium phosphate, carnallite ($KMgCl_3 \cdot 6(H_2O)$), and combinations thereof.

Embodiment 27: The device of any one of Embodiments 1 to 26, wherein the device produces DHP when operated in a humidity is between 1% and 20% relative humidity.

Embodiment 28: A method of preparing a dry hydrogen peroxide (DHP) containing environment comprising: providing a device comprising an electrically conductive network coated with a catalyst and an electrical power source that provides an electrical potential to said electrically conductive network according to any one of Embodiments 1 to 27; providing a flow of humid air through said electrically conductive network to prepare a DHP containing airflow; directing said DHP containing airflow in to an enclosed environment.

Embodiment 29: The method of Embodiment 28, wherein said environment accumulates DHP at a level of between 1 part-per-billion (ppb) and 200 ppb.

The present disclosure further includes, and provides for, devices having electrically conductive network coated with a catalyst as illustrated in FIGS. 8 to 14 wherein the conductive layer 125, adhesive layer 130, catalyst layer 135, and non-conductive layer 140 comprise the materials as provided in Tables 4 to 6. As will be understood by persons of skill in the art in view of the present disclosure, each of conductive layer 125, Adhesive layer 130, catalyst layer 135, and non-conductive layer 140 may further include additional components such as buffers and solvents as long as the materials do not change the overall property of an electrical conductivity and catalysis.

TABLE 4

Electrical Conductive Network Embodiments having
high performance, low cost, and availability

| Embodiment # | Configuration of certain electrical conductive networks |
|---|---|
| 4.1 | Conductive Layer: stainless steel<br>Adhesive Layer: (3-mercaptopropyl)triethoxysilane<br>Electrocatalytic Layer: $TiO_2$ (anatase) |
| 4.2 | Conductive Layer: aluminum<br>Conductive Layer #2: electroless nickel layer<br>Adhesive Layer: (3-mercaptopropyl)triethoxysilane<br>Electrocatalytic Layer: $TiO_2$ (anatase) |
| 4.3 | Non-Conductive Layer: polyethylene terephthalate<br>Conductive Layer: electroless nickel layer<br>Adhesive Layer: (3-mercaptopropyl)triethoxysilane<br>Electrocatalytic Layer: $TiO_2$ (anatase) |
| 4.4 | Conductive Layer: stainless steel<br>Adhesive Layer: (3-mercaptopropyl)trimethoxysilane<br>Electrocatalytic Layer: $TiO_2$ (anatase) |
| 4.5 | Conductive Layer: aluminum<br>Conductive Layer #2: electroless nickel layer<br>Adhesive Layer: (3-mercaptopropyl)trimethoxysilane<br>Electrocatalytic Layer: $TiO_2$ (anatase) |
| 4.6 | Non-Conductive Layer: polyethylene terephthalate<br>Conductive Layer: electroless nickel layer<br>Adhesive Layer: (3-mercaptopropyl)trimethoxysilane<br>Electrocatalytic Layer: $TiO_2$ (anatase) |
| 4.7 | Non-Conductive Layer: high density polypropylene<br>Conductive Layer: electroless nickel layer<br>Adhesive Layer: (3-mercaptopropyl)triethoxysilane<br>Electrocatalytic Layer: $TiO_2$ (anatase) |
| 4.8 | Non-Conductive Layer: high density polypropylene<br>Conductive Layer: electroless nickel layer<br>Adhesive Layer: (3-mercaptopropyl)trimethoxysilane<br>Electrocatalytic Layer: $TiO_2$ (anatase) |
| 4.9 | Non-Conductive Layer: high density polyethylene<br>Conductive Layer: electroless nickel layer<br>Adhesive Layer: (3-mercaptopropyl)triethoxysilane<br>Electrocatalytic Layer: $TiO_2$ (antase) |
| 4.10 | Non-Conductive Layer: high density polyethylene<br>Conductive Layer: electroless hickel layer<br>Adhesive Layer: (3-mercaptopropyl)trimethoxysilane<br>Electrocatalytic Layer: $TiO_2$ (anatase) |
| 4.11 | Conductive Layer: stainless steel<br>Adhesive Layer: (3-mercaptopropyl)triethoxysilane<br>Electrocatalytic Layer: $TiO_2$ (rutile) |
| 4.12 | Conductive Layer: aluminum<br>Conductive Layer #2: electroless nickel layer<br>Adhesive Layer: (3-mercaptopropyl)triethoxysilane<br>Electrocatalytic Layer: $TiO_2$ (rutile) |

TABLE 4-continued

Electrical Conductive Network Embodiments having
high performance, low cost, and availability

| Embodiment # | Configuration of certain electrical conductive networks |
|---|---|
| 4.13 | Non-Conductive Layer: polyethylene terephthalate<br>Conductive Layer: electroless nickel layer<br>Adhesive Layer: (3-mercaptopropyl)triethoxysilane<br>Electrocatalytic Layer: $TiO_2$ (rutile) |
| 4.14 | Conductive Layer: stainless steel<br>Adhesive Layer: (3-mercaptopropyl)trimethoxysilane<br>Electrocatalytic Layer: $TiO_2$ (rutile) |
| 4.15 | Conductive Layer: aluminum<br>Conductive Layer #2: electroless nickel layer<br>Adhesive Layer: (3-mercaptopropyl)trimethoxysilane<br>Electrocatalytic Layer: $TiO_2$ (rutile) |
| 4.16 | Non-Conductive Layer: polyethylene terephthalate<br>Conductive Layer: electroless nickel layer<br>Adhesive Layer: (3-mercaptopropyl)trimethoxysilane<br>Electrocatalytic Layer: $TiO_2$ (rutile) |
| 4.17 | Non-Conductive Layer: high density polypropylene<br>Conductive Layer: electroless nickel layer<br>Adhesive Layer: (3-mercaptopropyl)triethoxysilane<br>Electrocatalytic Layer: $TiO_2$ (rutile) |
| 4.18 | Non-Conductive Layer: high density polypropylene<br>Conductive Layer: electroless nickel layer<br>Adhesive Layer: (3-mercaptopropyl)trimethoxysilane<br>Electrocatalytic Layer: $TiO_2$ (rutile) |
| 4.19 | Non-Conductive Layer: high density polyethylene<br>Conductive Layer: electroless nickel layer<br>Adhesive Layer: (3-mercaptopropyl)triethoxysilane<br>Electrocatalytic Layer: $TiO_2$ (antase) |
| 4.20 | Non-Conductive Layer: high density polyethylene<br>Conductive Layer: electroless hickel layer<br>Adhesive Layer: (3-mercaptopropyl)trimethoxysilane<br>Electrocatalytic Layer: $TiO_2$ (rutile) |

TABLE 5

Electrical Conductive Network Embodiments
having high performance and availabilty

| Embodiment # | Configuration of certain electrical conductive networks |
|---|---|
| 5.1 | Conductive Layer: copper<br>Conductive Layer #2: electroless nickel layer<br>Adhesive Layer: (3-mercaptopropyl)triethyoxysilane<br>Electrocatalytic Layer: $TiO_2$ (anatase) |
| 5.2 | Conductive Layer: copper<br>Conductive Layer #2: electroless nickel layer<br>Adhesive Layer: (3-mercaptopropyl)trimethoxysilane<br>Electrocatalytic Layer: $TiO_2$ (anatase) |
| 5.3 | Conductive Layer: silver<br>Conductive Layer #2: electroless nickel layer<br>Adhesive Layter: (3-mercaptopropyl)triethoxysilane<br>Electrocatalytic Layer: $TiO_2$ (anatase) |
| 5.4 | Conductive Layer: silver<br>Conductive Layer #2: electroless nickel layer<br>Adhesive Layer: (3-mercaptopropyl)trimethoxysilane<br>Electrocatalytic Layer: $TiO_2$ (anatase) |
| 5.5 | Conductive Layer: copper<br>Conductive Layer #2: electroplated nickel layer<br>Adhesive Layer: (3-mercaptopropyl)triethoxysilane<br>Electrocatalytic Layer: $TiO_2$ (anatase) |
| 5.6 | Conductive Layer: copper<br>Conductive Layer #2: electroplated nickel layer<br>Adhesive Layer: (3-mercaptopropyl)trimethoxysilane<br>Electrocatalytic Layer: $TiO_2$ (anatase) |
| 5.7 | Conductive Layer: copper<br>Adhesive Layer: (3-mercaptopropyl)triethoxysilane<br>Electrocatalytic Layer: $TiO_2$ (anatase) |
| 5.8 | Conductive Layer: copper<br>Electrocatalytic Layer: $TiO_2$ (anatase) |
| 5.9 | Conductive Layer: copper<br>Conductive Layer #2: electroless nickel layer<br>Adhesive Layer: (3-mercaptopropyl)triethyoxysilane<br>Electrocatalytic Layer: $TiO_2$ (rutile) |

TABLE 5-continued

Electrical Conductive Network Embodiments
having high performance and availabilty

| Embodiment # | Configuration of certain electrical conductive networks |
|---|---|
| 5.10 | Conductive Layer: copper |
| | Conductive Layer #2: electroless nickel layer |
| | Adhesive Layer: (3-mercaptopropyl)trimethoxysilane |
| | Electrocatalytic Layer: TiO$_2$ (rutile) |
| 5.11 | Conductive Layer: silver |
| | Conductive Layer #2: electroless nickel layer |
| | Adhesive Layter: (3-mercaptopropyl)triethoxysilane |
| | Electrocatalytic Layer: TiO$_2$ (rutile) |
| 5.12 | Conductive Layer: silver |
| | Conductive Layer #2: electroless nickel layer |
| | Adhesive Layer: (3-mercaptopropyl)trimethoxysilane |
| | Electrocatalytic Layer: TiO$_2$ (rutile) |
| 5.13 | Conductive Layer: copper |
| | Conductive Layer #2: electroplated nickel layer |
| | Adhesive Layer: (3-mercaptopropyl)triethoxysilane |
| | Electrocatalytic Layer: TiO$_2$ (rutile) |
| 5.14 | Conductive Layer: copper |
| | Conductive Layer #2: electroplated nickel layer |
| | Adhesive Layer: (3-mercaptopropyl)trimethoxysilane |
| | Electrocatalytic Layer: TiO$_2$ (rutile) |
| 5.15 | Conductive Layer: copper |
| | Adhesive Layer: (3-mercaptopropyl)triethoxysilane |
| | Electrocatalytic Layer: TiO$_2$ (rutile) |
| 5.16 | Conductive Layer: copper |
| | Electrocatalytic Layer: TiO$_2$ (rutile) |

TABLE 6

Further Electrical Conductive Network Embodiments

| Embodiment # | Configuration of certain electrical conductive networks |
|---|---|
| 6.1 | Non-Conductive Layer: cotton |
| | Conductive Layer: electroless nickel layer |
| | Adhesive Layer: (3-mercaptopropyl)triethoxysilane |
| | Electrocatalytic Layer: TiO$_2$ (anatase) |
| 6.2 | Non-Conductive Layer: cotton |
| | Conductive Layer: electroless nickel layer |
| | Adhesive Layer: (3-mercaptopropyl)trimethoxysilane |
| | Electrocatalytic Layer: TiO$_2$ (anatase) |
| 6.3 | Non-Conductive Layer: cotton |
| | Conductive Layer: electroless nickel layer |
| | Electrocatalytic Layer: TiO$_2$ (anatase) |
| 6.4 | Non-Conductive Layer: cotton |
| | Conductive Layer: electroless nickel layer |
| | Adhesive Layer: (3-mercaptopropyl)triethoxysilane |
| | Electrocatalytic Layer: TiO$_2$ (rutile) |
| 6.5 | Non-Conductive Layer: cotton |
| | Conductive Layer: electroless nickel layer |
| | Adhesive Layer: (3-mercaptopropyl)trimethoxysilane |
| | Electrocatalytic Layer: TiO$_2$ (rutile) |
| 6.6 | Non-Conductive Layer: cotton |
| | Conductive Layer: electroless nickel layer |
| | Electrocatalyst: TiO$_2$ (rutile) |
| 6.7 | Conductive Layer: stainless steel |
| | Electrocatalytic Layer: TiO$_2$ (anatase) |
| 6.8 | Conductive Layer: aluminum |
| | Conductive Layer #2: electroless nickel layer |
| | Electrocatalytic Layer: TiO$_2$ (anatase) |
| 6.9 | Non-Conductive Layer: polyethylene terephthalate |
| | Conductive Layer: electroless nickel layer |
| | Electrocatalytic Layer: TiO$_2$ (anatase) |
| 6.10 | Conductive Layer: stainless steel |
| | Electrocatalytic Layer: TiO$_2$ (anatase) |
| 6.11 | Conductive Layer: aluminum |
| | Conductive Layer #2: electroless nickel layer |
| | Electrocatalytic Layer: TiO$_2$ (anatase) |

TABLE 6-continued

Further Electrical Conductive Network Embodiments

| Embodiment # | Configuration of certain electrical conductive networks |
|---|---|
| 6.12 | Non-Conductive Layer: polyethylene terephthalate |
| | Conductive Layer: electroless nickel layer |
| | Electrocatalytic Layer: TiO$_2$ (anatase) |
| 6.13 | Non-Conductive Layer: high density polypropylene |
| | Conductive Layer: electroless nickel layer |
| | Electrocatalytic Layer: TiO$_2$ (anatase) |

While the present disclosure has been described with reference to preferred embodiments, it will be understood by those skilled in the art that various changes may be made and equivalents may be substituted for elements thereof to adapt to particular situations without departing from the scope of the present disclosure. Therefore, it is intended that the present disclosure not be limited to the particular embodiments disclosed as the best mode contemplated for carrying out the present disclosure, but that the present disclosure will include all embodiments falling within the scope and spirit of the appended claims.

EXAMPLES

Example 1: Measurement of DHP

Hydrogen peroxide gas may be measured in a volume of air either directly using a gas analyzer such as a Portable Analyzer (4000 Series) produced by the Interscan Corporation. For example the Interscan 4090-1999b provides for detection of DHP down to a concentration of 1 part-per-billion (ppb).

Alternatively, a method to measure the amount of hydrogen peroxide over time or a method employing a calibrated pump are employed. To measure DHP over time, a hydrogen peroxide test strip normally used to measure approximate concentrations in aqueous solution is be used to detect the presence of DHP. The hydrogen peroxide test strip measures the accumulated DHP up to one hour to provide approximate readings of DHP concentration accurate to within 0.01 ppm. A test strip exposed for 15 twenty-second intervals accumulates 0.5 ppm over the course of five minutes indicating an approximate concentration of 0.033 ppm (e.g., 0.5 ppm divided by 15). To measure DHP using a calibrated pump, a known volume of air is drawn and provided to a Draeger tube (Draeger Ozone 0.05/b tube part #6733181), designed to detect hydrogen peroxide concentrations as low as 0.10 ppm. Drawing 2000 cubic centimeters of air using the calibrated pump, provides readings of lower concentrations accurate within 0.005 ppm using larger volumes of air for measurement. Larger volumes of air provide for the detection of lower overall concentrations of DHP. A measurement of 4000 cubic centimeters provides for the measurement of a DHP concentration of 0.05 ppm. A measurement of 4000 cubic centimeters provides for the measurement of a DHP concentration of 0.033 ppm.

Example 2: Preparation of Copper Mesh Sail

A copper mesh (AMACO Brent Impression Mesh, Copper ⅛", wire diameter: 0.0065", OA %: approx. 83%) is cute into a 6.375 inch diameter circle and two 22 AWG stranded wires are soldered onto opposite sides of the copper mesh circle. The copper sail is washed with warm soapy water, then rinsed with water. The mesh is rinsed with acetone and allowed to dry before a final thorough rinsing with deionized water. A coating of a solution of titanium dioxide ($TiO_2$) (NYACOL TiSol A, titanium dioxide and water, CAS No. 13463-67-7, lot No. 75-077-A) is applied with a clean paintbrush and allowed to dry. A second coat of $TiO_2$ is applied in the same manner and allowed to dry completely. Images of a coated copper mesh sail are shown in FIG. 1A to 1E.

Example 3: DHP Testing Setup

Testing for DHP production is performed in a glove box (Terra Universal Glovebox, internal volume 27.76 ft³). The glove box includes sensors for the measurement of temperature and relative humidity (Fischer Scientific Traceable Thermo-Hygro, Temperature and Relative Humidity sensor, Catalog No. 11-661-7D), a volatile organic compound (VOC) detector (Tiger LT VOC Meter 10.6 eV Krypton PID Lamp), and ozone detector (Drager Ozone 0.05/b tube part #6733181 with a Drager Accuro pump).

A line drawing of a modified a DHP generating device is presented in FIG. 2A to 2E. The DHP generating device is similar to a device discloses in WO 2018/129537 at FIG. 19, and is modified to remove the UV light and to replace the standard sail with either a $TiO_2$ coated copper mesh sail or an uncoated sail copper mesh sail. The sails either powered by a 9V battery or a DC power supply (Keithley DC power supply m/n: 2260B-30-36 360 W). An anemometer is installed into the round duct of the DHP gas assembly (Fieldpiece In-Duct Hot wire anemometer model STA2) and the resulting modified Synexis stand-alone DHP generating device is placed into the glovebox. The glove box is prepared for testing by placing a de-ionized (DI) water/salt solution in a tray to provide for and maintain a relative humidity level of between 65% to 75%. The output of the detectors is collected using an Onset HOBO UX120-006M data logger. The glove box portholes are open to the environment.

Example 4: DHP Testing Procedure

DHP production is performed using the setup of Example 3. Briefly, the glove box is prepared for testing by placing a de-ionized (DI) water/salt solution in a tray to provide for and maintain a relative humidity level of between 65% to 75%. The Interscan sensor is switched to sample mode (pump is one) and a C12 carbon scrubbing filter is attached to the inlet port. The HOBO data logger is attached to the data port on the Interscan sensor and turned on. Experimental setup and the Interscan sensor are run to allow the system to stabilize. During the stabilization period, VOC readings are obtained inside the glovebox and in the ambient area and ozone levels are measure inside the glovebox. The glovebox portholes are sealed off while the DHP generating device fan is running without an installed sail. Once the Interscan readings have stabilized (about 20 minutes), the C12 filter is removed and a PTFE sample tube is connected from the inlet port of the Interscan sensor to a port on the glove box.

To establish a baseline DHP level of the glovebox the sensor is allowed to measure the glovebox for 20 minutes without a sail inserted into the modified DHP generating device.

To begin testing the sail is inserted into the modified DHP generating device and energized by either connecting the electrodes to a standard 9V battery or to a Keithley DC power supply (m/n: 2260B-30-36 360 W) and the glovebox resealed. The test is run for a designated period of time and the data from the various sensors recorded on the data logger. At the end of the test period, the sample tube is disconnected from the Interscan and the C12 filter is reattached to the sensor inlet for about 20 minutes to determine whether and the amount the zero point drifted. The HOBO logger is turned off to complete the test.

Figure 3:
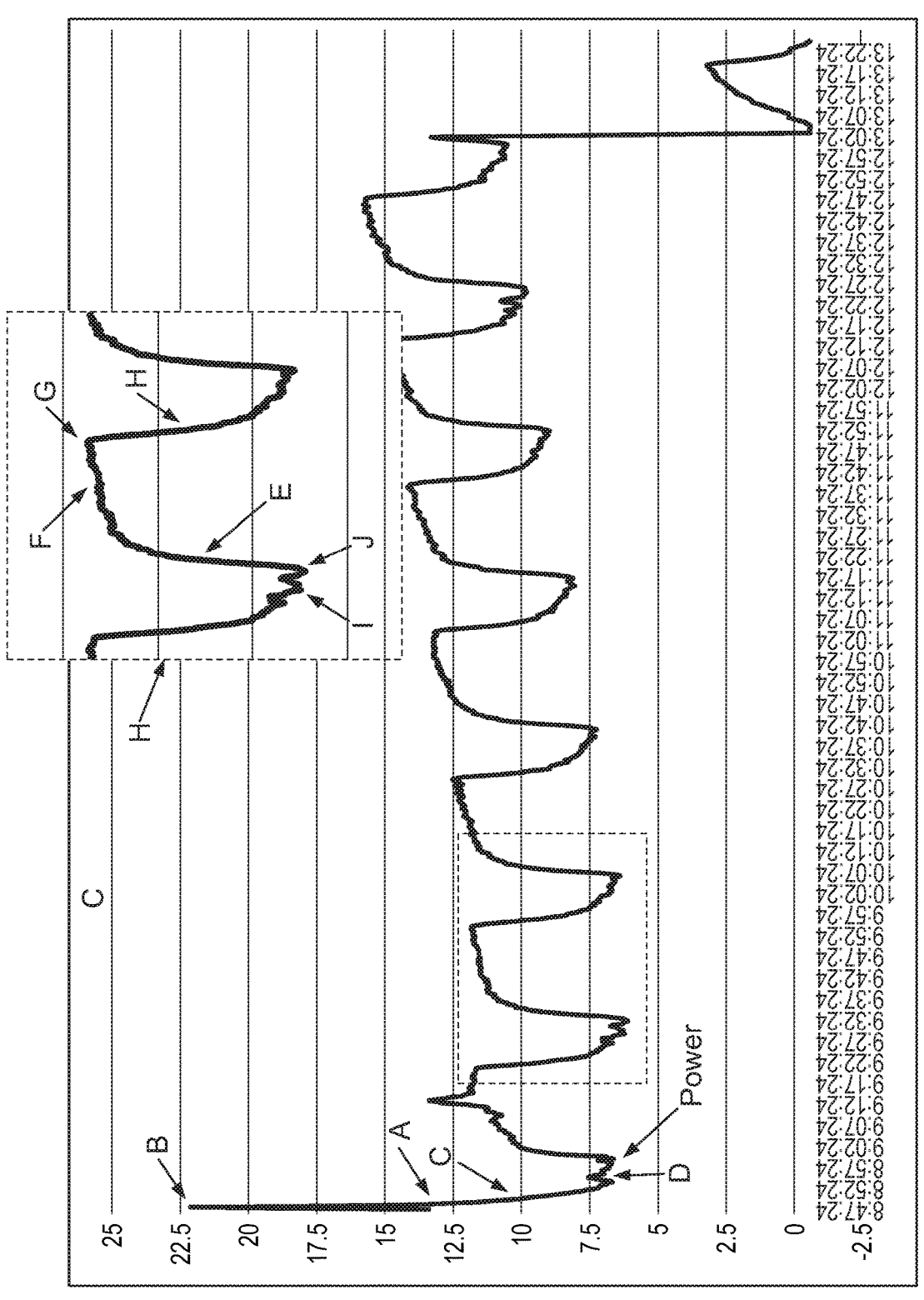
FIG. 3 is a plot of the levels of DHP in ppb versus time during the use of a electrocatalytic device comprising a catalyst coated electrically conductive network in a DHP device of the present disclosure.

Example 5: DHP Test Results a. Electrolytic production of DHP on $TiO_2$ coated copper mesh (5%) powered by a 9V Battery A $TiO_2$ coated copper mesh is prepared according to Example 2 and tested as described above. A plot of the level of DHP detected is plotted versus time in FIG. 3. The amount of coverage of the copper mesh is estimated at ab out 5%. The relative humidity is maintained between 68% to 70% and the temperature is 75° C. The test is initiated by the removal of the C-12 filter from the Interscan device (A) which results in a pressure spike (B) which decays (C) to background (D). The sail is powered by connection to a 9V battery (arrow) and DHP is detected and the level rises I. After a period, production of DHP plateaus (F) for a time before forced shift (G) occurs that results in decreasing levels of DHP (G) until DHP reaches a minima (I) before a second forces shift occurs and DHP levels rise again (E). The cycle is then repeated oscillating between the production of a slightly increasing maximum (F) and minimum (I) due to drift in the Interscan detector. At the plateau, DHP levels are measured about 5 ppb above the minima.

Not to be limited by theory, during electrocatalytic production of DHP, only one half-reaction dominates at a time. In one mode (cathodic phase), cathodic oxidation occurs generating hydroxyl ions which combine to form DHP. The DHP level rises (E) and peaks (F), maintaining a level of about 5 ppb DHP. A forced shift (G) occurs and the device enters a second mode (the "anodic phase"). During the anodic phase the DHP level drops (H) and reaches a minimum (I). During the anodic phase, it is thought that anodic reduction takes place wherein $H^+$ that was produced during the cathodic phase combines with oxygen to produce DHP. As discussed above, side reactions can consume DHP and these predominate when DHP is present. During anodic phase, DHP production is exceeded by the destruction of existing DHP. When provided with air that does not contain DHP, DHP is produced during both cathodic and anodic phases (not shown).

b. Electrolytic Production of DHP on Requires $TiO_2$

Figure 4:
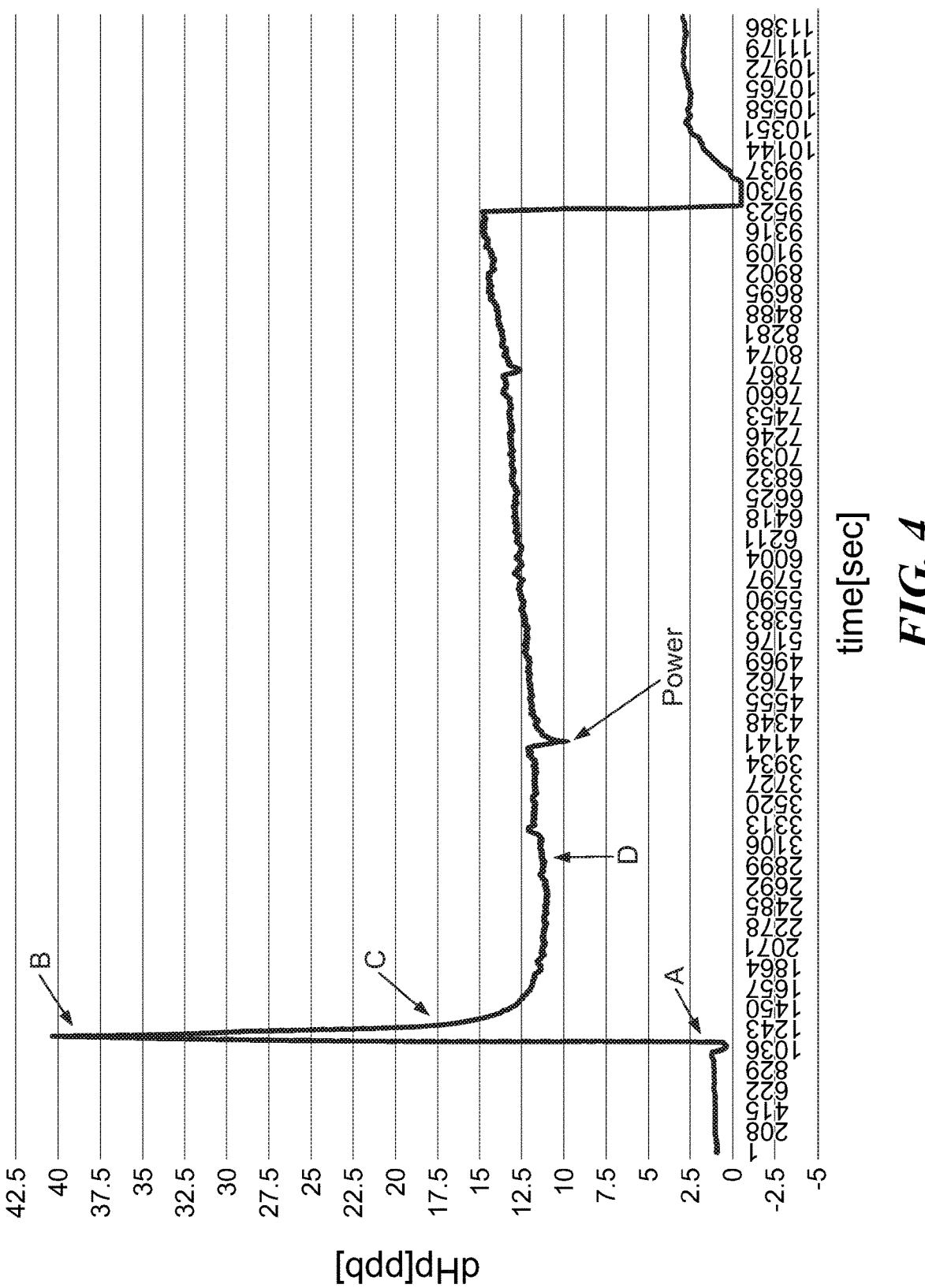
FIG. 4 is a plot of the levels of DHP of a device of the present disclosure having an uncoated conductive network of the present disclosure.
Figure 5:
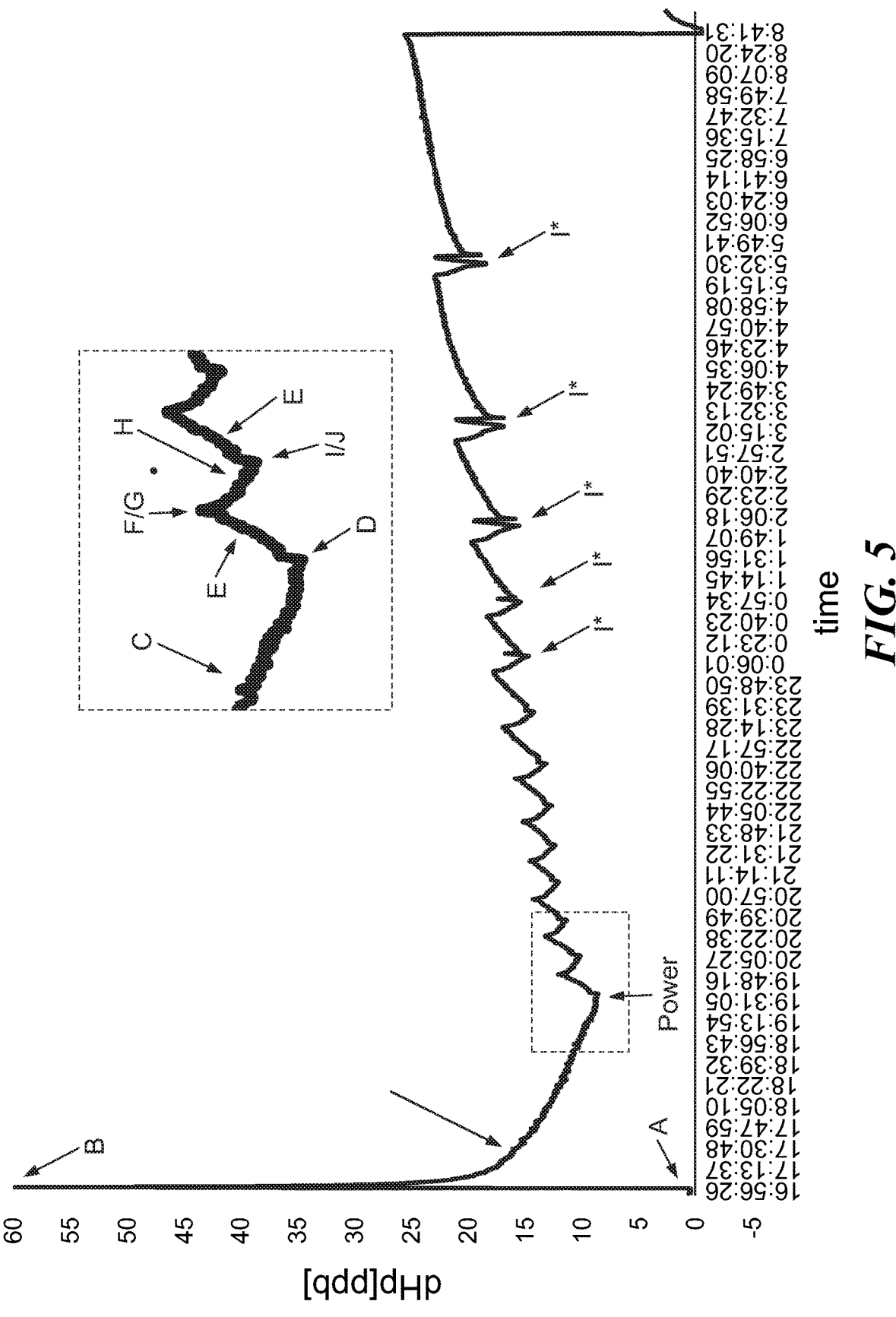
FIG. 5 is a plot of the levels of DHP in ppb versus time during the use of a electrocatalytic device comprising a catalyst coated electrically conductive network in a DHP device of the present disclosure.

The coated copper mesh is replaced with an uncoated copper mesh and tested using the methods described above. The relative humidity is maintained between 68% to 70% and the temperature is 75° C. As shown in FIG. 4, the removal of the C-12 filter from the Interscan device results in a pressure spike (B) which decays (C) to background (D). The uncoated sail is powered by connection to a 9V battery (arrow) however no rise in DHP levels are observed. In contrast to the coated copper mesh, no oscillating cycle is observed nor any drift on the Interscan device that is commonly observed.

c. Electrolytic Production of DHP on $TiO_2$ Coated Copper Mesh (>80%) DC Powered 0.5 A/0.3V A $TiO_2$ coated copper mesh is prepared according to Example 2 and tested as described above. A plot of the level of DHP detected is plotted versus time in FIG. 5. The amount of coverage of the copper mesh is estimated at >80% and the DC power source is set to run at a constant 0.5 Amps. The voltage is measured at 0.3 V. The relative humidity is maintained between 68% to 70% and the temperature is 75°

C. The test is initiated by the removal of the C-12 filter from the Interscan device (A) which results in a pressure spike (B) which decays (C) to background (D). The sail is powered by connection to a 9V battery (arrow) and DHP is detected and the level rises (E). After a period and in contrast to Example 5a, production of DHP plateaus (F) and immediately undergoes a forced shift (G). DHP levels decrease (H) and reach a minima (I) before a second forces shift occurs and DHP levels rise again (E'). Like the 5% coated sale at 9V, DHP levels oscillate, however by the seventh cycle, a decrease in the slope of the cathodic phase is observed and the length of time increases. At later cycles, during the minima phase, a prominent spike (I*) is observed. During the course of the test, both the peak and minima DHP levels rise, reaching a level of about 20 ppb by the end of the test.

Example 6: Analysis of Electrocatalytic Reaction in Copper/TiO$_2$ System

During testing, a number of unexpected changes to the catalyst and conductive mesh were observed. As shown in FIG. 1A, TiO$_2$ is a white crystal. The TiO$_2$ is applied to a copper mesh by dipping a copper mesh into a container containing a suspension of TiO$_2$. As shown in FIG. 1B, crystals remaining in the container adopt a bluish-green tint. The TiO$_2$ applied to the copper mesh adopt a very clear blue color as shown in FIG. 1C. Notably the now blue crystals of TiO$_2$ of FIG. 1C have not had an applied voltage. After applying a voltage as provided in Example 5a (e.g., 9V for x hours) the appearance of the crystals adhering to the copper mesh change to a paler blue and appears more transluscent (FIG. 1D). TiO$_2$ is removed from the used sail and observed to have a translucent blue color as shown in FIG. 1E.

The changes of the TiO$_2$ observed indicate the formation of Cupric Oxide (CuO) on the titanium dioxide where it is in contact with the copper mesh. This is evident from the development of a distinct green tint on the titanium dioxide crystals (FIGS. 1B, 1C and 1D). Microscopic examination indicates that there is no formation of either copper metal aggregates (plating) or of discrete cupric oxide crystals. Rather, the cupric oxide is being incorporated into the titanium dioxide crystals in a gradually aggregating surface layer. This is beneficial because cupric oxide actually has a lower band gap (1.21 eV to 1.51 eV) and is thus more conductive, than titanium dioxide (3.2 eV to 3.35 eV). See Srivastava et al., "Synthesis and Characterisation of Copper Oxide nanoparticles," IOSR Journal of Applied Physics 5(4):61-65 (2013). The spontaneous formation of a more conductive intermediate metal oxide species between the metal substrate and the titanium dioxide catalyst was completely unexpected.

Example 7: Preparation of Electrocatalytic Meshes

Electrocatalytic meshes are prepared from either conductive mesh substrates or non-conductive mesh substrates as illustrated in FIGS. 9 to 14.

In a first example, a stainless steel mesh of 0.125" diameter wire cut to a 6.375" diameter circle is washed with warm, soapy water before rinsing with deionized water. The mesh is then rinsed with acetone and allowed to dry before placing it in a $3 \times 10^{-3}$ M solution of (3-mercaptopropyl)triethoxysilane (Millipore-Sigma, CAS #14814-09-6) dissolved in ethanol. The wire mesh is dipped and dried three times. After this, the mesh is then coated with a solution of TiO$_2$ (NYACOL TiSol A, CAS #13463-67-7) via application with a brush. This is allowed to dry before repeating the process. The dried mesh is then sintered at 150° C. for 1 hour to ensure that the catalyst adheres to the mesh.

In a second example, a polyethylene terephthalate mesh of 0.125" diameter cut to a 6.375" diameter circle is washed with warm, soapy water before rinsing with deionized water. The mesh is then rinsed with acetone and allowed to dry before placing it in an electroless nickel plating solution (Millipore-Sigma) for 10 minutes. The mesh is removed and dried and then rinsed with deionized water two times before drying again. The mesh is then placed in a $3 \times 10^{-3}$ M solution of (3-mercaptopropyl)triethoxysilane (Millipore-Sigma, CAS #14814-09-6) dissolved in ethanol. The wire mesh is dipped and dried three times. After this, the mesh is then coated with a solution of TiO$_2$ (NYACOL TiSol A, CAS #13463-67-7) via application with a brush. This is allowed to dry before repeating the process. The dried mesh is then sintered at 150° C. for 1 hour to ensure that the catalyst adheres to the mesh.

The invention claimed is:

1. An electrocatalytic device for the production of dry hydrogen peroxide (DHP), said device comprising:
   a) an electrically conductive network coated with an electrocatalyst, wherein said electrocatalyst comprises one or more materials chosen from titanium dioxide, zinc oxide, iron oxide, or tungsten oxide; and
   b) a Modulated Alternating Current (MAC) electrical power source configured to provide an electric current and/or a voltage to said electrically conductive network,
   wherein said MAC electrical power source is configured to alternately initiate said electrocatalyst into a cathodic DHP operation mode and an anodic DHP operation mode by adjusting said electrical current and/or said voltage applied to said electrically conductive network,
   wherein during said cathodic DHP operation mode, said electrocatalyst acts as a cathode to generate DHP and wherein during said anodic DHP operation mode, said electrocatalyst acts as an anode to generate DHP,
   wherein said electrocatalytic device is configured to direct said DHP generated out of said electrocatalytic device and into a surrounding environment,
   wherein said electrically conductive network is an air permeable conductive network,
   wherein said air permeable conductive network comprises a meshwork or a conductive fabric, and
   wherein said air permeable conductive network has an electrocatalyst thickness of between 5 nm and 750 nm and an open area of between 10% and 60%.

2. The electrocatalytic device of claim 1, further comprising a fan for providing air flow into and through said device.

3. The electrocatalytic device of claim 2, further comprising an enclosure and wherein said fan, said electrically conductive network, and said MAC electrical power source are disposed within said enclosure.

4. The electrocatalytic device of claim 1, wherein said air permeable conductive network comprises a meshwork and said meshwork comprises a metal selected from the group consisting of copper, annealed copper, silver, gold, aluminum, tungsten, zinc, nickel, iron, platinum, tin, titanium, grain oriented electrical steel, stainless steel, and nichrome.

5. The electrocatalytic device of claim 4, wherein said meshwork comprises copper.

6. The electrocatalytic device of claim 1, wherein said air permeable conductive network comprises a meshwork and said meshwork comprises graphite.

7. The electrocatalytic device of claim 1, wherein said electrically conductive network has a resistivity ($\rho$) between $1.5 \times 10^{-8}$ ohm-meter ($\Omega \cdot m$) and $3 \times 10^{-3}$ ohm-meter ($\Omega \cdot m$) at 20° C.

8. The electrocatalytic device of claim 1, wherein said electrically conductive network has a conductivity (o) between $6.3 \times 10^7$ Siemens per meter (S/m) and $1 \times 10^5$ S/m at 20° C.

9. The electrocatalytic device of claim 1, wherein said air permeable conductive network comprises a conductive fabric and said conductive fabric is a woven or non-woven fabric.

10. The electrocatalytic device of claim 9, wherein said conductive fabric is a metal coated fabric comprising nylon and/or polyester coated with a metal selected from the group consisting of copper, annealed copper, silver, gold, aluminum, tungsten, zinc, nickel, iron, platinum, tin, titanium, grain oriented electrical steel, stainless steel, and nichrome.

11. The electrocatalytic device of claim 1, wherein said MAC electrical power source is configured to provide a voltage between 0.001 Volts (V) and 50,000 V.

12. The electrocatalytic device of claim 1, wherein said MAC electrical power source is configured to provide an electrical current having an amperage between 0.01 Amp (A) and 100 A.

13. The electrocatalytic device of claim 1, wherein said air permeable conductive network comprises a meshwork or a conductive fabric having a mesh of at least 100 cells (spaces) per square inch (cpsi).

14. The electrocatalytic device of claim 1, wherein said air permeable conductive network comprises a meshwork or a conductive fabric having a nominal hole size ranging from 50 microns to 1200 microns.

15. The electrocatalytic device of claim 1, wherein said titanium dioxide is in the form of anatase or rutile.

16. The electrocatalytic device of claim 1, wherein said tungsten oxide is tungsten (III) oxide, tungsten (IV) oxide ($WO_2$), tungsten (VI) oxide ($WO_3$), or tungsten pentoxide.

17. The electrocatalytic device of claim 1, wherein said electrocatalyst further comprises a co-catalyst selected from platinum, gold, silver, copper, nickel, cesium, palladium, rhodium, ruthenium, osmium, or iridium.

18. The electrocatalytic device of claim 1, wherein said electrocatalyst further comprises a hygroscopic additive selected from the group consisting of sodium hydroxide, potassium hydroxide, magnesium hydroxide, zinc chloride, calcium chloride, magnesium chloride, sodium phosphate, potassium phosphate, magnesium phosphate, carnallite ($KMgCl_3 \cdot 6(H_2O)$), and combinations thereof.

19. The electrocatalytic device of claim 1, wherein said device is installed in a heating, ventilation, and air conditioning (HVAC) system.

20. The electrocatalytic device of claim 1, wherein the device does not include a UV light source.

21. An electrocatalytic device for the production of dry hydrogen peroxide (DHP), said device comprising:
an enclosure including an inlet opening, an outlet opening, and a frame located between the inlet and outlet openings;
an electrically conductive network at least partially coated with a catalyst to form a catalyst-coated electrically conductive network,
wherein the electrically conductive network is formed from copper and wherein the catalyst comprises titanium dioxide,
wherein the catalyst-coated electrically conductive network has a thickness of between 1 micron and 7 mm and an open area of between 10% and 60%,
wherein the frame is configured to secure the catalyst-coated electrically conductive network between the inlet opening and the outlet opening such that air flowing between the inlet opening and the outlet opening during operation of the electrocatalytic device passes through the open area of the catalyst-coated electrically conductive network; and
a modulated alternating current (MAC) electrical power source, wherein the MAC electrical power source is coupled to the electrically conductive network and configured to provide electrical power to the catalyst-coated electrically conductive network when the electrocatalytic device is in operation,
wherein the catalyst-coated electrically conductive network, the inlet opening, and the outlet opening are arranged with a morphology that enables the removal of near-ideal gas phase DHP from the electrocatalytic device before the DHP is forced to undergo subsequent reduction or oxidation.

22. The electrocatalytic device of claim 21, wherein the enclosure is a duct of a heating, air conditioning, and ventilation (HVAC) system.

23. A method of preparing a dry hydrogen peroxide (DHP) containing environment, said method comprising:
providing said electrocatalytic device of claim 1;
providing a flow of humid air through said electrically conductive network of said electrocatalytic device to prepare a DHP containing airflow; and
directing said DHP containing airflow out of said electrocatalytic device and into an enclosed environment.

24. The method of claim 23, wherein said enclosed environment accumulates DHP at a level of between 1 part-per-billion (ppb) and 200 ppb.

\* \* \* \* \*